US012655201B2

(12) United States Patent
Sun et al.

(10) Patent No.: US 12,655,201 B2
(45) Date of Patent: Jun. 16, 2026

(54) ISOLATED ANTIGEN BINDING PROTEIN BINDING TO A COMPLEMENT PROTEIN C5 AND A METHOD OF DETECTING THEREOF

(71) Applicant: LONGBIO PHARMA (SUZHOU) CO., LTD., Shanghai (CN)

(72) Inventors: Nai-Chau Sun, Shanghai (CN); Chow-Rou-Yun Sun, Shanghai (CN); Qi Gao, Shanghai (CN); Haili Ma, Shanghai (CN); Heng Liu, Shanghai (CN)

(73) Assignee: LONGBIO PHARMA (SUZHOU) CO., LTD., Shanghai (CN)

( * ) Notice: Subject to any disclaimer, the term of this patent is extended or adjusted under 35 U.S.C. 154(b) by 687 days.

(21) Appl. No.: 18/000,661

(22) PCT Filed: Jun. 4, 2021

(86) PCT No.: PCT/CN2021/098261
§ 371 (c)(1),
(2) Date: Dec. 2, 2022

(87) PCT Pub. No.: WO2021/244627
PCT Pub. Date: Dec. 9, 2021

(65) Prior Publication Data
US 2023/0212272 A1     Jul. 6, 2023

(30) Foreign Application Priority Data
Jun. 5, 2020     (CN) ......................... 202010507896.8

(51) Int. Cl.
| | |
|---|---|
| *C07K 16/18* | (2006.01) |
| *A61K 38/17* | (2006.01) |
| *A61K 39/395* | (2006.01) |
| *A61K 47/68* | (2017.01) |
| *A61K 49/00* | (2006.01) |
| *C07K 14/47* | (2006.01) |
| *C07K 16/00* | (2006.01) |
| *G01N 33/68* | (2006.01) |

(52) U.S. Cl.
CPC .......... *C07K 16/18* (2013.01); *A61K 38/1725* (2013.01); *A61K 39/395* (2013.01); *A61K 39/39516* (2013.01); *A61K 47/6843* (2017.08); *A61K 49/00* (2013.01); *C07K 14/472* (2013.01); *C07K 16/00* (2013.01); *G01N 33/6893* (2013.01); *C07K 2317/24* (2013.01); *C07K 2317/565* (2013.01); *C07K 2317/76* (2013.01); *C07K 2317/92* (2013.01); *G01N 2333/4716* (2013.01); *G01N 2800/347* (2013.01)

(58) Field of Classification Search
CPC ............ C07K 2317/76; C07K 2317/24; C07K 16/18; C07K 2317/21; C07K 2317/55; C07K 2317/565; C07K 2317/54; C07K 2317/56; C07K 2319/00; C07K 2317/515; C07K 14/472; C07K 2317/567; A61K 39/39533; A61K 29/00; A61P 25/00; A61P 25/28
See application file for complete search history.

(56) References Cited

U.S. PATENT DOCUMENTS

| | | | |
|---|---|---|---|
| 8,241,628 B2 | 8/2012 | Diefenbach-Streiber et al. | |
| 8,883,158 B2 | 11/2014 | Diefenbach-Streiber et al. | |
| 9,011,852 B2 * | 4/2015 | Rother ...................... | A61P 7/06 424/133.1 |
| 9,079,949 B1 | 7/2015 | Andrien, Jr. et al. | |
| 9,107,861 B1 | 8/2015 | Andrien, Jr. et al. | |
| 9,206,251 B2 | 12/2015 | Andrien, Jr. et al. | |
| 9,221,901 B2 * | 12/2015 | Rother ................... | A61P 37/06 |
| 9,309,310 B2 * | 4/2016 | Rother ................... | A61P 37/02 |
| 9,371,377 B2 | 6/2016 | Andrien, Jr. et al. | |
| 9,701,743 B2 | 7/2017 | Baciu et al. | |
| 9,932,395 B2 | 4/2018 | Baciu et al. | |
| 10,584,164 B2 | 3/2020 | Andrien, Jr. et al. | |
| 10,633,434 B2 | 4/2020 | Hu et al. | |
| 10,752,678 B2 | 8/2020 | Baciu et al. | |
| 2016/0031975 A1 | 2/2016 | Diefenbach-Streiber et al. | |
| 2016/0251433 A1 | 9/2016 | Andrien, Jr. et al. | |
| 2017/0260260 A1 | 9/2017 | Diefenbach-Streiber et al. | |
| 2017/0298123 A1 | 10/2017 | Andrien, Jr. et al. | |
| 2020/0262900 A1 | 8/2020 | Hu et al. | |

(Continued)

FOREIGN PATENT DOCUMENTS

| | | |
|---|---|---|
| CN | 104177495 A | 12/2014 |
| CN | 107207585 A | 9/2017 |

(Continued)

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*

(Continued)

*Primary Examiner* — Chang-Yu Wang
(74) *Attorney, Agent, or Firm* — Merchant & Gould P.C.; Daniel J. Pereira

(57) ABSTRACT

An isolated antigen binding protein, which includes at least one CDR of a heavy chain variable region and at least one CDR of a light chain variable region and a method to encode an isolated nucleic acid molecule. A vector with the nucleic acid molecule. A cell with the nucleic acid molecule. A pharmaceutical composition with the isolated antigen binding protein. A method for preventing, alleviating or treating a C5-related disease or disorder. A method for detecting C5 in a sample.

15 Claims, 4 Drawing Sheets

Specification includes a Sequence Listing.

(56) References Cited

U.S. PATENT DOCUMENTS

| | | | |
|---|---|---|---|
| 2020/0262901 | A1 | 8/2020 | Hu et al. |
| 2020/0385481 | A1 | 12/2020 | Song et al. |
| 2021/0101965 | A1 | 4/2021 | Baciu et al. |

FOREIGN PATENT DOCUMENTS

| | | | | |
|---|---|---|---|---|
| CN | 109563159 A | 4/2019 | | |
| CN | 110603054 A | 12/2019 | | |
| WO | WO-2011137395 A1 * | 11/2011 | ................ | A61P 7/04 |
| WO | WO-2017062649 A1 * | 4/2017 | .............. | A61P 27/02 |
| WO | WO-2018075761 A1 * | 4/2018 | ........... | G01N 33/564 |
| WO | WO-2018081400 A1 * | 5/2018 | ........... | G01N 33/502 |

OTHER PUBLICATIONS

Rudikoff et al., Proc. Natl. Acad. Sci. USA 1982 vol. 79: p. 1979.*
International Search Report issued Sep. 9, 2023 in PCT/CN2021/098261, 7 pages.
Floch et al., "Treatment of Delayed Hemolytic Transfusion Reactions in Sickle Cell Disease Patients By an Anti-C5 Antibody", Blood, vol. 134, Nov. 13, 2019, p. 2458.

* cited by examiner

ISOLATED ANTIGEN BINDING PROTEIN BINDING TO A COMPLEMENT PROTEIN C5 AND A METHOD OF DETECTING THEREOF

This application is a National Stage Application and claims priority under 35 U.S.C. § 371 to Patent Cooperation Treaty application PCT/CN2021/098261, filed Jun. 4, 2021, which claims the benefit of CN application CN2020105078968, filed Jun. 5, 2020. Priority is claimed to these applications and the disclosures of these prior applications are considered part of the disclosure of this application and to the extent allowed the entire contents of the aforementioned applications are incorporated herein.

SEQUENCE LISTING

In accordance with 37 CFR § 1.52(e)(5) and with 37 CFR § 1.831, the specification makes reference to a Sequence Listing submitted electronically as a .TXT file named Sequence-Listing-19684.0073FPWO.txt, which is 41,000 bytes in size. The entire contents of the Sequence Listing are hereby incorporated by reference.

TECHNICAL FIELD

The present application relates to the field of biomedicine, and specifically to an isolated antigen binding protein and a use thereof.

BACKGROUND OF THE INVENTION

A complement system plays a critical role in the innate immune response. The complement system consists of more than 25 plasma proteins which function through three currently known activation pathways: a classical pathway, a lectin pathway, and an alternative pathway. Although these pathways differ in their initial steps, they share the same late complement components (C5 to C9) responsible for activating and destroying target cells.

A complement system with normal functions can provide a potent defense against microbial infection, while complement dysregulation may also lead to the occurrence of various disorders. For example, paroxysmal nocturnal hemoglobinuria (PNH), which arises from a mutation in the PIG-A gene of hematopoietic stem cells causing the loss of a group of membrane proteins anchored to the cell surface through glycosylphosphatidylinositol (GPI), thereby leading to changes in the properties of cells. Its clinical manifestations include bone marrow failure and thrombosis in addition to complement-mediated chronic intravascular hemolysis. It is revealed from the results of a large-scale clinical epidemiological survey that the mortality rate of PNH patients is 35% within 5 years post-diagnosis, and the mortality rate is 50% within 10 years post-diagnosis. Thrombotic events are the leading cause of death in PNH patients in Europe and the United States, accounting for approximately 40-67%.

There are two main types of treatment for PNH, symptom-based symptomatic treatment and hematopoietic stem cell transplantation. The latter is used only in patients with severe PNH with aplastic anemia or those who have progressed to leukemia. The drugs currently approved by the FDA for the treatment of PNH include Eculizumab (Trade Name: Soliris®) and Ravulizumab-cwvz (Trade Name: Ultomiris), whose therapeutic effects, however, need to be further improved. Therefore, it is still very necessary to study and develop other therapeutics.

SUMMARY OF THE INVENTION

The present application provides an isolated antigen binding protein, including at least one CDR of a heavy chain variable region and at least one CDR of a light chain variable region, wherein the heavy chain variable region includes an amino acid sequence as shown in any one of SEQ ID NOs: 44-46 or a variant thereof, and the light chain variable region includes an amino acid sequence as shown in SEQ ID NO: 70 or a variant thereof.

In some embodiments, the variant of the amino acid sequence as shown in SEQ ID NO: 70 includes an amino acid mutation selected from a group consisting of: D32E, D32I, D32L, D32G, D32S, D32T, D32V, D32Y, G33A, G33S, G33I, G33Q, G33T and G33V.

In some embodiments, the isolated antigen binding protein includes an HCDR1 of the heavy chain variable region with its amino acid sequence as shown in any one of SEQ ID NOs: 44-46.

In some embodiments, the isolated antigen binding protein includes an HCDR2 of the heavy chain variable region with its amino acid sequence as shown in any one of SEQ ID NOs: 44-46.

In some embodiments, the isolated antigen binding protein includes an HCDR3 of the heavy chain variable region with its amino acid sequence as shown in any one of SEQ ID NOs: 44-46.

In some embodiments, the HCDR1 includes an amino acid sequence as shown in SEQ ID NO: 18.

In some embodiments, the HCDR2 includes an amino acid sequence as shown in SEQ ID NO: 19.

In some embodiments, the HCDR3 includes an amino acid sequence as shown in SEQ ID NO: 20.

In some embodiments, the isolated antigen binding protein includes an LCDR1 of the light chain variable region with the amino acid sequence as shown in any one of SEQ ID NOs: 41-43.

In some embodiments, the isolated antigen binding protein includes an LCDR2 of the light chain variable region with the amino acid sequence as shown in any one of SEQ ID NOs: 41-43.

In some embodiments, the isolated antigen binding protein includes an LCDR3 of the light chain variable region with the amino acid sequence as shown in any one of SEQ ID NOs: 41-43.

In some embodiments, the LCDR1 includes an amino acid sequence as shown in SEQ ID NO: 69.

In some embodiments, the LCDR1 includes an amino acid sequence as shown in any one of SEQ ID NOs: 1 and 2.

In some embodiments, the LCDR2 includes an amino acid sequence as shown in SEQ ID NO: 16.

In some embodiments, the LCDR3 includes an amino acid sequence as shown in SEQ ID NO: 17.

In some embodiments, the isolated antigen binding protein includes an antibody or an antigen binding fragment thereof.

In some embodiments, the antigen binding fragment includes Fab, Fab', F(ab)2, an Fv fragment, F(ab')2, scFv, di-scFv and/or dAb.

In some embodiments, the light chain variable region includes framework regions L-FR1, L-FR2, L-FR3, and L-FR4.

In some embodiments, a C-terminus of the L-FR1 is directly or indirectly linked to an N-terminus of the LCDR1, and the L-FR1 includes an amino acid sequence as shown in any one of SEQ ID NOs: 21-23.

In some embodiments, the L-FR1 includes an amino acid sequence as shown in any one of SEQ ID NOs: 21-23.

In some embodiments, the L-FR2 is located between the LCDR1 and the LCDR2, and the L-FR2 includes an amino acid sequence as shown in any one of SEQ ID NOs: 24-25.

In some embodiments, the L-FR2 includes an amino acid sequence as shown in any one of SEQ ID NOs: 24-25.

In some embodiments, the L-FR3 is located between the LCDR2 and the LCDR3, and the L-FR3 includes an amino acid sequence as shown in any one of SEQ ID NOs: 26-28.

In some embodiments, the L-FR3 includes an amino acid sequence as shown in any one of SEQ ID NOs: 26-28.

In some embodiments, an N-terminus of the L-FR4 is linked to a C-terminus of the LCDR3, and the L-FR4 includes an amino acid sequence as shown in any one of SEQ ID NOs: 29-30.

In some embodiments, the L-FR4 includes an amino acid sequence as shown in any one of SEQ ID NOs: 29-30.

In some embodiments, the light chain variable region includes an amino acid sequence as shown in any one of SEQ ID NOs: 41-43.

In some embodiments, the isolated antigen binding protein includes an antibody light chain constant region, and the antibody light chain constant region includes a human Kappa light chain constant region.

In some embodiments, the antibody light chain constant region includes an amino acid sequence as shown in SEQ ID NO: 47.

In some embodiments, the isolated antigen binding protein includes an antibody light chain, and the antibody light chain includes an amino acid sequence as shown in any one of SEQ ID NOs: 49, 51 and 53.

In some embodiments, the heavy chain variable region includes framework regions H-FR1, H-FR2, H-FR3, and H-FR4.

In some embodiments, a C-terminus of the H-FR1 is directly or indirectly linked to an N-terminus of the HCDR1, and the H-FR1 includes an amino acid sequence as shown in any one of SEQ ID NOs: 31-33.

In some embodiments, the H-FR1 includes an amino acid sequence as shown in any one of SEQ ID NOs: 31-33.

In some embodiments, the H-FR2 is located between the HCDR1 and the HCDR2, and the H-FR2 includes an amino acid sequence as shown in any one of SEQ ID NOs: 34-35.

In some embodiments, the H-FR2 includes an amino acid sequence as shown in any one of SEQ ID NOs: 34-35.

In some embodiments, the H-FR3 is located between the HCDR2 and the HCDR3, and the H-FR3 includes an amino acid sequence as shown in any one of SEQ ID NOs: 36-38.

In some embodiments, the H-FR3 includes an amino acid sequence as shown in any one of SEQ ID NOs: 36-38.

In some embodiments, an N-terminus of the H-FR4 is linked to a C-terminus of the HCDR3, and the H-FR4 includes an amino acid sequence as shown in any one of SEQ ID NOs: 39-40.

In some embodiments, the H-FR4 includes an amino acid sequence as shown in any one of SEQ ID NOs: 39-40.

In some embodiments, the heavy chain variable region includes an amino acid sequence as shown in any one of SEQ ID NOs: 44-46.

In some embodiments, the isolated antigen binding protein includes an antibody heavy chain constant region, and the antibody heavy chain constant region is derived from a human IgG heavy chain constant region.

In some embodiments, the isolated antigen binding protein includes an antibody heavy chain constant region, and the antibody heavy chain constant region is derived from a human IgG1 heavy chain constant region.

In some embodiments, the antibody heavy chain constant region includes an amino acid sequence as shown in SEQ ID NO: 48.

In some embodiments, the isolated antigen binding protein includes an antibody heavy chain, and the antibody heavy chain includes an amino acid sequence as shown in any one of SEQ ID NOs: 50, 52 and 54.

In some embodiments, the antigen is C5.

In some embodiments, the C5 is a human C5.

In another aspect, the present application further provides an isolated nucleic acid molecule, which encodes the isolated antigen binding protein of the present application.

In another aspect, the present application further provides a vector, which includes the nucleic acid molecule of the present application.

In another aspect, the present application further provides a cell, which includes the nucleic acid molecule of the present application or the vector of the present application.

In another aspect, the present application further provides a method for preparing the isolated antigen binding protein of the present application, which includes culturing the cell of the present application under conditions allowing the expression of the isolated antigen binding protein of the present application.

In another aspect, the present application further provides a pharmaceutical composition, which comprises the isolated antigen binding protein of the present application, the nucleic acid molecule of the present application, the vector of the present application and/or the cell of the present application, and optionally a pharmaceutically acceptable adjuvant.

In another aspect, the present application further provides use of the isolated antigen binding protein, the nucleic acid molecule, the vector, the cell, and/or the pharmaceutical composition of the present application in the preparation of a medicament for preventing, alleviating and/or treating a C5-related disease or disorder.

In another aspect, the present application further provides a method for preventing, alleviating or treating a C5-related disease or disorder, which includes administering to a subject in need thereof the isolated antigen binding protein, the nucleic acid molecule, the vector, the cell, and/or the pharmaceutical composition of the present application.

In another aspect, the present application further provides the isolated antigen binding protein, the nucleic acid molecule, the vector, the cell, and/or the pharmaceutical composition, which are used in the method for preventing, alleviating or treating a C5-related disease or disorder.

In another aspect, the present application further provides a method for detecting C5 in a sample, which includes administering the isolated antigen binding protein of the present application.

Additional aspects and advantages of the present disclosure will become readily apparent to those skilled in this art from the following detailed description, wherein only illustrative embodiments of the present disclosure are shown and described. As will be realized by those skilled in this art, the content of the present disclosure enables those skilled in the art to make changes to the disclosed specific embodiments without departing from the spirit and scope of the invention involved in this application. Accordingly, the drawings and description are to be regarded as illustrative in nature, and not as restrictive.

BRIEF DESCRIPTION OF THE DRAWING

The specific features of the present application are set forth in the appended claims. A better understanding of the features and advantages of the present application will be obtained by referring to the illustrative embodiments and the drawings described in detail below. A brief description of the drawings is as follows:

DETAILED DESCRIPTION

Figure 1:
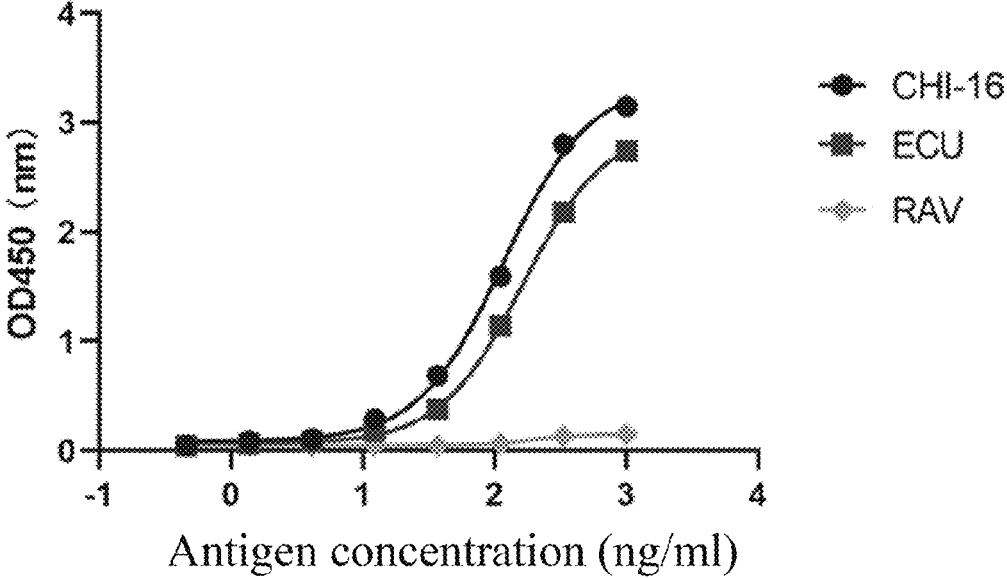
FIG. 1 shows the results of the antigen binding assay of the chimeric antibody of this application and the positive control antibody.

The implementation of the present application will be illustrated in the following specific examples, and other advantages and effects of the present application will be easily known by those familiar with this technology from the content disclosed in the specification.

Definition of Terms

In the present application, the term "isolated" generally refers to artificially obtained from the natural state or synthesized artificially. If a certain "isolated" substance or component occurs in nature, it may be due to a change in its natural environment, or the substance may be isolated from its natural environment, or both. For example, a certain non-isolated polynucleotide or polypeptide naturally exists in a living animal, and the same polynucleotide or polypeptide isolated from such a natural state is called isolated. The term "isolated" does not exclude being mixed with artificial or synthetic substances, nor does it exclude the presence of other impure substances that do not affect the activity of the substance.

In the present application, the term "isolated nucleic acid molecule" generally refers to isolated nucleotides, deoxyribonucleotides or ribonucleotides of any length, or analogues thereof isolated from its natural environment or synthesized artificially.

In the present application, the term "variant" generally refers to molecules with amino acid modifications (such as, group substitutions, etc.) or with insertion, substitution, and/or deletion of one or more amino acids on the original protein sequence, while retaining the function of the original sequence. For example, the variant may have better biological activity (or function) than the original sequence. For example, the reservation need not be a complete reservation. For example, the variant can substantially retain the function of the original sequence, for example, at least 50%, 60%, 65%, 70%, 75%, 80%, 85%, 90%, 95%, 96%, 97%, 98%, or 99% the function of the original sequence is retained. For example, the amino acid sequence of the variant can be at least 70%, 75%, 80%, 85%, 90%, 95%, 96%, 97%, 98%, or 99% identical to the original amino acid sequence. For example, the variants of the amino acid sequence as shown in SEQ ID NO: 69 can include molecules with amino acid modifications (such as, group substitutions, etc.) or with insertion, substitution, and/or deletion of one or more amino acids on the amino acid sequence as shown in SEQ ID NO: 1, while retaining the function of the original sequence. For example, the function of the amino acid sequence as shown in SEQ ID NO: 1 can be substantially retained, e.g., at least 50%, 60%, 65%, 70%, 75%, 80%, 85%, 90%, 95%, 96%, 97%, 98%, or 99% of the function of the amino acid sequence as shown in SEQ ID NO: 1 is retained. For example, it can be at least 70%, 75%, 80%, 85%, 90%, 95%, 96%, 97%, 98%, or 99% identical to the amino acid sequence as shown in SEQ ID NO: 1. In the present application, identity can be determined, for example, by the Needleman-Wunsch algorithm (Needleman and Wunsch, 1970, J. Mol. Biol. 48: 443-453) implemented in the Needle program v3.0.0 or later of the EMBOSS software package (EMBOSS: European Molecular Biology Open Software Suite, Rice et, al., 2000, Trends in Genetics 16: 276-277). The optional parameters used are gap penalty 10, gap extension penalty 0.5 and EBLOSUM62 substitution matrix (EMBOSS version of BLOSUM62). The output of "longest identity" labeled with Needle is used as the identity percentage, and calculated as follows: (identical residues×100)/ (length of alignment−total number of gaps in the alignment).

In the present application, the term "isolated antigen binding protein" generally refers to a protein with antigen binding ability obtained artificially from the native state or artificially synthesized. The "isolated antigen binding protein" may include an antigen binding portion and optionally, a scaffold or framework portion that allows the antigen binding portion to adopt a conformation that facilitates the antigen binding portion to bind to the antigen. The antigen binding protein may include, for example, an antibody-derived protein scaffold or alternative protein scaffolds or artificial scaffolds with grafted CDRs or CDR derivatives. Such scaffolds include, but are not limited to, antibody-derived scaffolds containing mutations introduced, for example, to stabilize the three-dimensional structure of the antigen binding protein, and fully synthetic scaffolds containing, for example, biocompatible polymers. See, for example, Korndorfer et al, 2003, Proteins: Structure, Function, and Bioinformatics, 53(1):121-129 (2003); Roque et al, Biotechnol. Prog. 20:639-654 (2004). In addition, peptide antibody mimics ("PAMs") and scaffolds based on antibody mimics using fibronectin components can also be used as the scaffolds.

In the present application, the term "antibody" generally refers to an immunoglobulin or a fragment or derivative thereof, encompassing any polypeptides that include an antigen binding site, no matter whether it is produced in vitro or in vivo. The term includes, but is not limited to, polyclonal, monoclonal, mono-specific, multi-specific, nonspecific, humanized, single-stranded, chimeric, synthetic, recombinant, hybrid, mutated and grafted antibodies. Unless otherwise modified by a term "complete", as in "complete antibody", for the purposes of the present invention, the term "antibody" also includes antibody fragments, such as Fab, F(ab')2, Fv, scFv, Fd, dAb and other antibody fragments that retain the function of antigen binding (e.g., specifically binding to human C5). In general, such fragments should include antigen binding domains. For example, a basic 4-chain antibody unit is a heterotetrameric glycoprotein composed of two identical light (L) chains and two identical heavy (H) chains. For example, an IgM antibody is composed of 5 basic heterotetrameric units and another polypeptide called J chain; while an IgA antibody includes 2-5 basic 4-chain units that can be polymerized with the J chain to form a multivalent combination. In terms of IgG, the 4-chain unit is generally about 150,000 Daltons. Each L chain is linked to the H chain through a covalent disulfide bond, while two H chains are linked to each other through one or more disulfide bonds depending on the isotype of the H chain. Each H and L chain also has regularly spaced intra-chain disulfide bridges. Each H chain may have a variable domain/variable region (VH) at the N-terminus, which is followed by three constant domains/constant regions (CHs) for each of α and γ chains, and followed by four CH domains for μ and ε isotypes. Each L chain may have a variable domain/variable region (VL) at the N-terminus, and may have a constant domain/constant region (CL) at the other terminus. In some embodiments, VL corresponds to VH, and CL corresponds to the first constant domain (CH1) of the heavy chain. Specific amino acid residues are considered to form an interface between the light chain and heavy chain variable domains. VH may be paired with VL to form an antigen binding site. For the structures and properties of different kinds of antibodies, see for example Basic and Clinical Immunology, 8th Edition, Daniel P. Sties, Abba I. Terr and Tristram G. Parsolw (eds), Appleton & Lange, Norwalk, Conn., 1994, Page 71 and Chapter 6. In some embodiments, L chains from any vertebrate species can be classified into one of two distinct types based on the amino acid sequence of their constant domains, called kappa and lambda. Depending on the amino acid sequence of its heavy chain constant domain/constant region (CH), immunoglobulin can be classified into different types or isotypes. There are five types of immune globulin: IgA, IgD, IgE, IgG and IgM, which have heavy chains named α, δ, ε, γ and μ, respectively. Based on the relatively small differences in terms of CH sequences and functions, the γ and α types are further divided into sub-types. For example, human contains the following subtypes: IgG1, IgG2A, IgG2B, IgG3, IgG4, IgA1 and IgK1.

In the present application, the term "antigen binding fragment" generally refers to a portion of a full-length antibody (e.g., a target binding region or a variable region) or a functional fragment or analog thereof. The examples of antibody fragments can include Fab, Fab', F(ab')2 and Fv fragments, etc. A "Functional fragment or analog" generally refer to a compound having substantially the same qualitative biological activity as a full-length antibody. For example, the functional fragment or analog of an anti-C5 antibody can bind to C5 protein, thereby inhibiting the hemolysis in the classical pathway and/or alternative pathway. An "Fv" fragment is generally the smallest antibody fragment that contains a complete target recognizing and binding site. This region may be composed of a dimer containing a heavy chain variable domain non-covalently linked to a light chain variable domain (VH-VL dimer).

In the present application, the term "framework region" generally refers to the portion of the variable region of an antibody known in the art that exists between the more variable (i.e., hypervariable) CDRs. Generally, such framework regions are typically known as frameworks 1 to 4 (FR1, FR2, FR3, and FR4), and provide a skeleton presenting six CDRs (three from the heavy chain, and three from the light chain) in the three-dimensional space, to form an antigen binding surface. That is, four in VH (H-FR1, H-FR2, H-FR3, and H-FR4), and four in VL (L-FR1, L-FR2, L-FR3, and L-FR4). For example, the VL of the isolated antigen binding protein of the present application can include framework regions L-FR1, L-FR2, L-FR3, and L-FR4. The VH of the isolated antigen binding protein of the present application can include framework regions H-FR1, H-FR2, H-FR3, and H-FR4.

In the present application, the term "variable" generally refers to the fact that there is a great difference in the sequences of some segments of the antibody variable regions (e.g., heavy chain variable regions, light chain variable regions) among antibodies. Generally, the variable region mediates the binding of an antigen and determines the specificity of a specific antibody to its specific antigen. Generally, variability is not evenly distributed throughout the variable domain. Instead, it is concentrated in several segments called complementary determining regions (CDRs) or hypervariable regions (HVRs) in the light chain and heavy chain variable domains. The relatively conserved portion of the variable region is referred to as framework region (FR). The variable domains of natural heavy chains and light chains each can include four FR regions, most of which are in β-folded configuration in which they are linked through three CDRs to form a part of the β-folded structure in some cases. The CDRs in each chain are held closely together through FR, and can promote the formation of the antigen binding site of the antibody together with the CDRs from another chain (see Kabat et al, Sequences of Immunological Interest, Fifth Edition, National Institute of Health, Bethesda, Md. (1991)). In general, the constant regions are not directly involved in the binding of antibodies to antigens, but exhibit various effector functions, for example, antibodies are involved in the antibody-dependent cytotoxicity.

In the present application, the term "light chain variable region" generally refers to the amino-terminal domain of the light chain of an antibody. The light chain variable region can be referred to as "VL". These domains are usually the most variable parts in the light chain of an antibody (relative to other antibodies of the same type), and they can include complementary determining regions (CDRs) or hypervariable regions (HVRs) and framework regions (FRs).

In the present application, the term "heavy chain variable region" generally refers to the amino-terminal domain of the heavy chain of an antibody. The heavy chain variable region can be referred to as "VH". These domains are usually the most variable parts in the heavy chain of an antibody (relative to other antibodies of the same type), and they can include complementary determining regions (CDRs) or hypervariable regions (HVRs) and framework regions (FRs).

In the present application, the term "subject" and "patient" can be used interchangeably, and generally refers to mammals, such as human patients and non-human primates, and experimental animals, such as rabbit, rat and mouse, as well as other animals. Animals include all the vertebrates, e.g., mammals and non-mammals, such as dog, cat, sheep, cow, pig, rabbit, chicken, etc. For example, the subjects for practicing the treatment method of the present application are humans. The subjects in need of treatment include patients who have already suffered from C5-related diseases or disorders and those predisposed to develop such disorders.

In this application, the term "prevention" generally refers to the prophylactic administration of the combination to healthy patients, in order to prevent the onset of the diseases and disorders described in this application. In addition, the term "prevention" refers to the prophylactic administration of such a combination to patients who are in the pre-stage of allergic diseases to be treated. The term "prevention" does not require 100% elimination of the probability of an event. More precisely, it means that the probability of an event is reduced in the presence of the pharmaceutical composition or method.

In the present application, the term "treatment" generally refers to administering or giving a therapeutic agent to a patient, or administering or giving the therapeutic agent to tissues or cell lines isolated from the patient suffering from a disease, having symptoms of a disease or having a tendency of a disease, with purposes of treating, curing, alleviating, relieving, changing, rescuing, improving, enhancing or affecting the disease, disease symptoms or disease tendency. It can include improving the disease state, eliminating the focus, or improving the prognosis.

In the present application, the term "cell" generally refers to a single cell, cell line, or cell culture that can be or has been a recipient of a nucleic acid molecule or a vector. The cells may include the nucleic acid molecules of the present invention or the vector of the present invention. The cells may include the offspring of a single cell. Due to natural, accidental or intentional mutations, the offspring may not necessarily be exactly the same as the original parent cell (in the form of the total DNA complement or in the genome). The cells can include cells transfected with the vector of the present invention in vitro. The cells can be bacterial cells (e.g., *E. coli*), yeast cells, or other eukaryotic cells, such as COS cells, Chinese Hamster Ovary (CHO) cells, HeLa cells, HEK293 cells, COS-1 cells, NS0 cells, or myeloma cells. In some embodiments, the cells are mammal cells. In some embodiments, the mammal cells are HEK293T cells.

In the present application, the term "pharmaceutical composition" generally refers to the composition suitable for administering to patients, e.g., human patients. For example, the pharmaceutical composition of the present application may include the isolated antigen binding protein of the present application, the vector of the present application and/or the cell of the present application, as well as optionally a pharmaceutically acceptable adjuvant. In addition, the pharmaceutical composition may also include one or more (pharmaceutically effective) carriers, stabilizers, excipients, diluents, solubilizers, surfactants, emulsifiers and/or preservatives and other suitable preparations. The acceptable ingredients of the composition may be non-toxic to the recipient at the dosage and concentration used. The pharmaceutical composition of the present application includes, but not limited to, liquid, frozen and freeze-dried compositions.

In the present application, the term "pharmaceutically acceptable adjuvant" generally refers to any and all solvents, dispersion media, coatings, isotonic agents and absorption delaying agents that are compatible with the medication, which are generally safe, non-toxic and neither biologically nor otherwise undesirable.

In the present application, the term "vector" generally refers to a nucleic acid delivery vehicle into which a polynucleotide encoding a certain protein can be inserted so as to enable the expression of the protein. The vector can make the genetic elements it carries be expressed in a host cell by transforming, transducing, or transfecting the host cell. For example, the vector includes: plasmid; phagemid; Cosmid; artificial chromosomes, such as yeast artificial chromosomes (YACs), bacterial artificial chromosomes (BACs) or P1-derived artificial chromosomes (PACs); phages, such as lambda phages or M13 phages and animal viruses, and the like. The species of animal viruses used as the vector are retrovirus (including lentivirus), adenovirus, adeno-associated virus, herpes virus (e.g., herpes simplex virus), poxvirus, baculovirus, papilloma virus, papovavirus (e.g., SV40). The vector may contain various elements for controlling the expression, including promoter sequences, transcription initiation sequences, enhancer sequences, selective elements and reporter genes. In addition, the vector may also contain replication initiation sites. The vector may also include ingredients that help its entry into cells, such as virion, lipidosome or protein coat, but not only these substances.

In the present application, the term "directly or indirectly linked" generally means "directly linked" or "indirectly linked" in relative terms. The "directly linked" generally means direct linkage. For example, the direct linkage can be the case where the linked substances (such as amino acid sequence segments) are directly linked without spacers (such as amino acid residues or derivatives thereof) between them. For example, an amino acid sequence segment X is directly linked to another amino acid sequence segment Y through an amide bond formed between the C-terminal amino acid of the amino acid sequence segment X and the N-terminal amino acid of the amino acid sequence segment Y. The indirect linkage can be the case where the linked substances (such as amino acid sequence segments) are indirectly linked with spacers (such as amino acid residues or derivatives thereof) between them. For example, in the isolated antigen binding protein of the present application, the C-terminus of L-FR1 can be directly or indirectly linked to the N-terminus of LCDR1.

In the present application, the term "complementary determining region" or the term "CDR" generally refers to amino acid sequences that collectively define the binding affinity and specificity of the variable regions of the binding site of an antigen binding protein (e.g., native immunoglobulin, chimeric antibody, or humanized antibody) (see for example, Chothia et, al., J. Mol. Biol. 196:901-917(1987); Kabat et, al., U.S. Dept of Health and Human Services NIH Publication No. 913242(1991)). In general, an antibody includes six CDRs; three in VH (HCDR1, HCDR2, HCDR3), and three in VL (LCDR1, LCDR2, LCDR3). Naturally occurring camel antibodies only composed of heavy chains function normally and stably in the absence of light chains. See for example, Hamers-Casterman et al., Nature 363:446-448 (1993); Sheriff et al, Nature Struct. Biol. 3:733-736 (1996).

In the present application, the term "C5", also called "complement component 5" or "complement factor 5" generally refers to complement cascade serum protein or variants thereof. The C5 protein can includes two chains, alpha and betta. This protein indicates the focal point involved in three complement activation pathways: the classical pathway, the alternative pathway, and the mannose-binding lectin pathway. The amino acid sequence of a full-length C5 protein cam be exemplified by the amino acid sequence provided in GenBank as accession number NP_001726.2. The term "C5" can include a recombinant C5 protein or fragment thereof. This term can also include a C5 protein or fragment thereof that binds, e.g., a histidine tag, a murine or human Fc, or a signal sequence (e.g., ROR1). For example, this term can include a sequence as exemplified in the sequence shown in SEQ ID NO: 60.

In the present application, the term "C5-related disease or disorder" generally refers to any disease or disorder that can be treated or alleviated by interfering with C5 protein. For example, complement-related diseases include inflammatory and autoimmune diseases, distal tissue injury following local ischemia and reperfusion, complement activation during cardiopulmonary bypass surgery, dermatomyositis, pemphigus, lupus nephritis, glomerulonephritis, renal vasculitis, cardiopulmonary bypass, heart failure-induced coronary endothelial dysfunction, type II membranoproliferative glomerulonephritis, acute renal failure, antiphospholipid syndrome, macular degeneration, endophthalmitis, novel vascular disease, allograft transplantation, hyperacute rejection, hemodialysis, chronic obstructive pulmonary disease (COPD) respiratory distress syndrome, asthma, paroxysmal nocturnal hemoglobinuria (PNH), and aspiration pneumonia, etc.

In the present application, the term "KD", also called "$K_D$", "affinity constant" or "equilibrium dissociation constant", generally refers to the value obtained at equilibrium in a titration measurement, or by dividing the dissociation rate constant (kd) by the association rate constant ($K_a$). The association rate constant ($K_a$), dissociation rate constant ($K_d$) and equilibrium dissociation constant ($K_D$) are used to represent the binding affinity of the binding protein (e.g., the isolated antigen binding protein of the present application) to the antigen (e.g., human C5). Methods for determining the association and dissociation rate constants are well known in the art. The use of a fluorescence-based technology provides high sensitivity and the ability to detect samples at equilibrium in physiological buffers. For example, the $K_D$ value can be determined through Octet, and can also be determined using other experimental approaches and instruments, such as BIAcore (Biomolecular Interaction Analysis). In addition, MesoScale Discovery Electrochemiluminescence Assay-Solution Equilibrium Titration (MSD-SET) is used to determine the $K_D$ value. This determination method is described in Estep P. et, al., MAbs, 2013. 5(2): p. 270-8.

In the present application, the term "comprising" or "including" generally means including expressly specified features, but not excluding other elements.

In the present application, the term "about" generally means varying in a range of 0.5%-10% above or below a specified value, for example, varying in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified value.

DETAILED DESCRIPTION OF THE INVENTION

Antigen Binding Protein

In one aspect, the present application provides an antigen binding protein. The antigen binding protein includes at least one CDR of the light chain variable region VL.

In the present application, the antigen binding protein can include LCDR1, and the LCDR1 can include an amino acid sequence as shown in SEQ ID NO: 69: KASQSVDYX$_9$X$_{10}$DSYLN (SEQ ID NO: 69): wherein, X$_9$=D, E, I, L, G, S, T, V or Y; X$_{10}$=G, A, S, I, Q, T or V. For example, said sequence can be a sequence determined according to Chothia definition rules.

In some cases, compared with the LCDR1 of the antigen binding protein as shown in SEQ ID NO: 1, said LCDR1 can include at least an amino acid substitution at a position selected from: an amino acid substitution at X$_9$ and/or X$_{10}$.

In some cases, compared with the LCDR1 of the antigen binding protein as shown in SEQ ID NO: 1, said LCDR1 can include at least an amino acid substitution at X$_9$ and/or X$_{10}$, wherein the amino acid at X$_9$ can be substituted for D, E, I, L, G, S, T, V, or Y; and the amino acid at X$_{10}$ can be substituted for G, A, S, I, Q, T, or V.

For example, the LCDR1 can include an amino acid sequence as shown in any one of SEQ ID NOs: 1-15.

In the present application, the antigen binding protein can include LCDR2, and the LCDR2 can include an amino acid sequence as shown in SEQ ID NO: 16.

In the present application, the antigen binding protein can include LCDR3, and the LCDR3 can include an amino acid sequence as shown in SEQ ID NO: 17.

In the present application, the antigen binding protein can include L-FR1, a C-terminus of the L-FR1 is directly or indirectly linked to an N-terminus of the LCDR1, and the L-FR1 can include an amino acid sequence as shown in any one of SEQ ID NOs: 21-23.

In the present application, the antigen binding protein can include L-FR2, the L-FR2 is located between the LCDR1 and the LCDR2, and the L-FR2 can include an amino acid sequence as shown in any one of SEQ ID NOs: 24-25.

In the present application, the antigen binding protein can include L-FR3, the L-FR3 is located between the LCDR2 and the LCDR3, and the L-FR3 can include an amino acid sequence as shown in any one of SEQ ID NOs: 26-28.

In the present application, the antigen binding protein can include L-FR4, an N-terminus of the L-FR4 is directly or indirectly linked to a C-terminus of the LCDR3, and the L-FR4 can include an amino acid sequence as shown in any one of SEQ ID NOs: 29-30.

In the present application, the antigen binding protein can include a light chain variable region VL, and the VL can include an amino acid sequence as shown in any one of SEQ ID NOs: 41-43.

In the present application, the antigen binding protein can include a light chain constant region CL, and the CL can include a human Kappa light chain constant region. For example, the CL can include an amino acid sequence as shown in SEQ ID NO: 47.

In the present application, the antigen binding protein can include a light chain, and the light chain can include an amino acid sequence as shown in any one of SEQ ID NOs: 49, 51 and 53.

The antigen binding protein includes at least one CDR of the heavy chain variable region VH.

In the present application, the antigen binding protein can include HCDR1, and the HCDR1 can include an amino acid sequence as shown in SEQ ID NO: 18.

In the present application, the antigen binding protein can include HCDR2, and the HCDR2 can include an amino acid sequence as shown in SEQ ID NO: 19.

In the present application, the antigen binding protein can include HCDR3, and the HCDR3 can include an amino acid sequence as shown in SEQ ID NO: 20.

In the present application, the antigen binding protein can include H-FR1, a C-terminus of the H-FR1 is directly or indirectly linked to an N-terminus of the HCDR1, and the H-FR1 can include an amino acid sequence as shown in any one of SEQ ID NOs: 31-33.

In the present application, the antigen binding protein can include H-FR2, the H-FR2 is located between the HCDR1 and the HCDR2, and the H-FR2 can include an amino acid sequence as shown in any one of SEQ ID NOs: 34-35.

In the present application, the antigen binding protein can include H-FR3, the H-FR3 is located between the HCDR2 and the HCDR3, and the H-FR3 can include an amino acid sequence as shown in any one of SEQ ID NOs: 36-38.

In the present application, the antigen binding protein can include H-FR4, an N-terminus of the H-FR4 is directly or indirectly linked to a C-terminus of the HCDR3, and the H-FR4 can include an amino acid sequence as shown in any one of SEQ ID NOs: 39-40.

In the present application, the antigen binding protein can include a heavy chain variable region VH, and the VH can include an amino acid sequence as shown in any one of SEQ ID NOs: 44-46.

In the present application, the antigen binding protein can include a heavy chain constant region CH, and the CH can include a human IgG heavy chain constant region. In some cases, the IgG heavy chain constant region can include a human IgG1 heavy chain constant region. For example, the CH can include an amino acid sequence as shown in SEQ ID NO: 48.

In the present application, the antigen binding protein can include a heavy chain, and the heavy chain can include an amino acid sequence as shown in any one of SEQ ID NOs: 50, 52 and 54.

In the present application, the antigen binding protein can include LCDR1-3, the LCDR1 can include an amino acid sequence as shown in SEQ ID NO: 69, the LCDR2 can include an amino acid sequence as shown in SEQ ID NO: 16, and the LCDR3 can include an amino acid sequence as shown in SEQ ID NO: 17.

In the present application, the antigen binding protein can include LCDR1-3, the LCDR1 can include an amino acid sequence as shown in any one of SEQ ID NOs: 1-15, the LCDR2 can include an amino acid sequence as shown in SEQ ID NO: 16, and the LCDR3 can include an amino acid sequence as shown in SEQ ID NO: 17.

For example, the antigen binding protein of the present application can include LCDR1-3 the same as those of CHI-16, the LCDR1 can include an amino acid sequence as shown in SEQ ID NO: 1, the LCDR2 can include an amino acid sequence as shown in SEQ ID NO: 16, and the LCDR3 can include an amino acid sequence as shown in SEQ ID NO: 17.

For example, the antigen binding protein of the present application can include LCDR1-3 the same as those of 16H1L2m and 16H46L39am, the LCDR1 can include an amino acid sequence as shown in SEQ ID NO: 2, the LCDR2 can include an amino acid sequence as shown in SEQ ID NO: 16, and the LCDR3 can include an amino acid sequence as shown in SEQ ID NO: 17.

In the present application, the antigen binding protein can include L-FR1-4, the L-FR1 can include an amino acid sequence as shown in any one of SEQ ID NOs: 21-23, the L-FR2 can include an amino acid sequence as shown in any one of SEQ ID NOs: 24-25, the L-FR3 can include an amino acid sequence as shown in any one of SEQ ID NOs: 26-28, and the L-FR4 can include an amino acid sequence as shown in any one of SEQ ID NOs: 29-30.

For example, the antigen binding protein of the present application can include L-FR1-4 the same as those of CHI-16, the L-FR1 can include an amino acid sequence as shown in SEQ ID NO: 21, the L-FR2 can include an amino acid sequence as shown in SEQ ID NO: 24, the L-FR3 can include an amino acid sequence as shown in SEQ ID NO: 26, and the L-FR4 can include an amino acid sequence as shown in SEQ ID NO: 29.

For example, the antigen binding protein of the present application can include L-FR1-4 the same as those of 16H1L2m, the L-FR1 can include an amino acid sequence as shown in SEQ ID NO: 22, the L-FR2 can include an amino acid sequence as shown in SEQ ID NO: 24, the L-FR3 can include an amino acid sequence as shown in SEQ ID NO: 27, and the L-FR4 can include an amino acid sequence as shown in SEQ ID NO: 30.

For example, the antigen binding protein of the present application can include L-FR1-4 the same as those of 16H46L39am, the L-FR1 can include an amino acid sequence as shown in SEQ ID NO: 23, the L-FR2 can include an amino acid sequence as shown in SEQ ID NO: 25, the L-FR3 can include an amino acid sequence as shown in SEQ ID NO: 28, and the L-FR4 can include an amino acid sequence as shown in SEQ ID NO: 30.

In the present application, the antigen binding protein can include HCDR1-3, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

For example, the antigen binding protein of the present application can include HCDR1-3 the same as those of CHI-16, 16H1L2m and 16H46L39am, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

In the present application, the antigen binding protein can include H-FR1-4, the H-FR1 can include an amino acid sequence as shown in any one of SEQ ID NOs: 31-33, the H-FR2 can include an amino acid sequence as shown in any one of SEQ ID NOs: 34-35, the H-FR3 can include an amino acid sequence as shown in any one of SEQ ID NOs: 36-38, and the H-FR4 can include an amino acid sequence as shown in any one of SEQ ID NOs: 39-40.

For example, the antigen binding protein of the present application can include H-FR1-4 the same as those of CHI-16, the H-FR1 can include an amino acid sequence as shown in SEQ ID NO: 31, the H-FR2 can include an amino acid sequence as shown in SEQ ID NO: 34, the H-FR3 can include an amino acid sequence as shown in SEQ ID NO: 36, and the H-FR4 can include an amino acid sequence as shown in SEQ ID NO: 39.

For example, the antigen binding protein of the present application can include H-FR1-4 the same as those of 16H1L2m, the H-FR1 can include an amino acid sequence as shown in SEQ ID NO: 32, the H-FR2 can include an amino acid sequence as shown in SEQ ID NO: 35, the H-FR3 can include an amino acid sequence as shown in SEQ ID NO: 37, and the H-FR4 can include an amino acid sequence as shown in SEQ ID NO: 40.

For example, the antigen binding protein of the present application can include H-FR1-4 the same as those of 16H46L39am, the H-FR1 can include an amino acid sequence as shown in SEQ ID NO: 33, the H-FR2 can include an amino acid sequence as shown in SEQ ID NO: 35, the H-FR3 can include an amino acid sequence as shown in SEQ ID NO: 38, and the H-FR4 can include an amino acid sequence as shown in SEQ ID NO: 40.

In the present application, the antigen binding protein can include LCDR1-3 and HCDR1-3, the LCDR1 can include an amino acid sequence as shown in SEQ ID NO: 69, the LCDR2 can include an amino acid sequence as shown in SEQ ID NO: 16, the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

In the present application, the antigen binding protein can include LCDR1-3 and HCDR1-3, the LCDR1 can include an amino acid sequence as shown in any one of SEQ ID NOs: 1-15, the LCDR2 can include an amino acid sequence as shown in SEQ ID NO: 16, the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

For example, the antigen binding protein of the present application can include LCDR1-3 and HCDR1-3 the same as those of CHI-16, the LCDR1 can include an amino acid sequence as shown in SEQ ID NO: 1, the LCDR2 can include an amino acid sequence as shown in SEQ ID NO: 16, the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

For example, the antigen binding protein of the present application can include LCDR1-3 and HCDR1-3 the same as those of 16H1L2m and 16H46L39am, the LCDR1 can include an amino acid sequence as shown in SEQ ID NO: 2, the LCDR2 can include an amino acid sequence as shown in SEQ ID NO: 16, and the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

In the present application, the antigen binding protein can include a light chain variable region VL and a heavy chain variable region VH, the VL can include an amino acid sequence as shown in any one of SEQ ID NOs: 41-43, and the VH can include an amino acid sequence as shown in any one of SEQ ID NOs: 44-46.

For example, the antigen binding protein can include a light chain variable region VL and a heavy chain variable region VH the same as those of CHI-16, the VL can include an amino acid sequence as shown in SEQ ID NO: 41, and the VH can include an amino acid sequence as shown in SEQ ID NO: 44.

For example, the antigen binding protein can include a light chain variable region VL and a heavy chain variable region VH the same as those of 16H1L2m, the VL can include an amino acid sequence as shown in SEQ ID NO: 42, and the VH can include an amino acid sequence as shown in SEQ ID NO: 45.

For example, the antigen binding protein can include a light chain variable region VL and a heavy chain variable region VH the same as those of 16H46L39am, the VL can include an amino acid sequence as shown in SEQ ID NO: 43, and the VH can include an amino acid sequence as shown in SEQ ID NO: 46.

In the present application, the antigen binding protein can include a light chain constant region CL and a heavy chain constant region CH, the CL can include an amino acid sequence as shown in SEQ ID NO: 47, and the CH can include an amino acid sequence as shown in SEQ ID NO: 48.

For example, the antigen binding protein can include a light chain constant region CL and a heavy chain constant region CH the same as those of CHI-16, 16H1L2m, and 16H46L39am, the CL can include an amino acid sequence as shown in SEQ ID NO: 47, and the CH can include an amino acid sequence as shown in SEQ ID NO: 48.

In the present application, the antigen binding protein can include a light chain and a heavy chain, the light chain can include an amino acid sequence as shown in any one of SEQ ID NOs: 49, 51 and 53, and the heavy chain can include an amino acid sequence as shown in any one of SEQ ID NOs: 50, 52 and 54.

For example, the antigen binding protein can include a light chain and a heavy chain the same as those of CHI-16, the light chain can include an amino acid sequence as shown in SEQ ID NO: 49, and the heavy chain can include an amino acid sequence as shown in SEQ ID NO: 50.

For example, the antigen binding protein can include a light chain and a heavy chain the same as those of 16H1L2m, the light chain can include an amino acid sequence as shown in SEQ ID NO: 51, and the heavy chain can include an amino acid sequence as shown in SEQ ID NO: 52.

For example, the antigen binding protein can include a light chain and a heavy chain the same as those of 16H46L39am, the light chain can include an amino acid sequence as shown in SEQ ID NO: 53, and the heavy chain can include an amino acid sequence as shown in SEQ ID NO: 54.

In the present application, the antigen binding protein can include LCDR1-3 and L-FR1-4, the LCDR1 can include an amino acid sequence as shown in SEQ ID NO: 1, the LCDR2 can include an amino acid sequence as shown in SEQ ID NO: 16, the LCDR3 can include an amino acid sequence as shown in SEQ ID NO: 17, the L-FR1 can include an amino acid sequence as shown in SEQ ID NO: 21, the L-FR2 can include an amino acid sequence as shown in SEQ ID NO: 24, the L-FR3 can include an amino acid sequence as shown in SEQ ID NO: 26, and the L-FR4 can include an amino acid sequence as shown in SEQ ID NO: 29; the antigen binding protein can also include VL and CL, the VL can include an amino acid sequence as shown in SEQ ID NO: 41, and the CL can include an amino acid sequence as shown in SEQ ID NO: 47; the antigen binding protein can also include HCDR1-3 and H-FR1-4, the HCDR1 can include an amino acid sequence as shown in SEQ ID NO: 18, the HCDR2 can include an amino acid sequence as shown in SEQ ID NO: 19, the HCDR3 can include an amino acid sequence as shown in SEQ ID NO: 20, the H-FR1 can include an amino acid sequence as shown in SEQ ID NO: 31, the H-FR2 can include an amino acid sequence as shown in SEQ ID NO: 34, the H-FR3 can include an amino acid sequence as shown in SEQ ID NO: 36, and the H-FR4 can include an amino acid sequence as shown in SEQ ID NO: 39; the antigen binding protein can also include VH and CH, the VH can include an amino acid sequence as shown in SEQ ID NO: 44, and the CH can include an amino acid sequence as shown in SEQ ID NO: 48; and the antigen binding protein can also include a light chain and a heavy chain, the light chain can include an amino acid sequence as shown in SEQ ID NO: 49, and the heavy chain can include an amino acid sequence as shown in SEQ ID NO: 50. For example, the antigen binding protein can include an antibody light chain and a heavy chain the same as those of CHI-16.

In the present application, the antigen binding protein can include LCDR1-3 and L-FR1-4, the LCDR1 can include an amino acid sequence as shown in SEQ ID NO: 2, the LCDR2 can include an amino acid sequence as shown in SEQ ID NO: 16, the LCDR3 can include an amino acid sequence as shown in SEQ ID NO: 17, the L-FR1 can include an amino acid sequence as shown in SEQ ID NO: 22, the L-FR2 can include an amino acid sequence as shown in SEQ ID NO: 24, the L-FR3 can include an amino acid sequence as shown in SEQ ID NO: 27, and the L-FR4 can include an amino acid sequence as shown in SEQ ID NO: 30; the antigen binding protein can also include VL and CL, the VL can include an amino acid sequence as shown in SEQ ID NO: 42, and the CL can include an amino acid sequence as shown in SEQ ID NO: 47; the antigen binding protein can also include HCDR1-3 and H-FR1-4, the HCDR1 can include an amino acid sequence as shown in SEQ ID NO: 18, the HCDR2 can include an amino acid sequence as shown in SEQ ID NO: 19, the HCDR3 can include an amino acid sequence as shown in SEQ ID NO: 20, the H-FR1 can include an amino acid sequence as shown in SEQ ID NO: 32, the H-FR2 can include an amino acid sequence as shown in SEQ ID NO: 35, the H-FR3 can include an amino acid sequence as shown in SEQ ID NO: 37, and the H-FR4 can include an amino acid sequence as shown in SEQ ID NO: 40; the antigen binding protein can also include VH and CH, the VH can include an amino acid sequence as shown in SEQ ID NO: 45, and the CH can include an amino acid sequence as shown in SEQ ID NO: 48; and the antigen binding protein can also include a light chain and a heavy chain, the light chain can include an amino acid sequence as shown in SEQ ID NO: 51, and the heavy chain can include an amino acid sequence as shown in SEQ ID NO: 52. For example, the antigen binding protein can include an antibody light chain and a heavy chain the same as those of 16H1L2m.

In the present application, the antigen binding protein can include LCDR1-3 and L-FR1-4, the LCDR1 can include an amino acid sequence as shown in SEQ ID NO: 2, the LCDR2 can include an amino acid sequence as shown in SEQ ID NO: 16, the LCDR3 can include an amino acid sequence as shown in SEQ ID NO: 17, the L-FR1 can include an amino acid sequence as shown in SEQ ID NO: 23, the L-FR2 can include an amino acid sequence as shown in SEQ ID NO: 25, the L-FR3 can include an amino acid sequence as shown in SEQ ID NO: 28, and the L-FR4 can include an amino acid sequence as shown in SEQ ID NO: 30; the antigen binding protein can also include VL and CL, the VL can include an amino acid sequence as shown in SEQ ID NO: 43, and the CL can include an amino acid sequence as shown in SEQ ID NO: 47; the antigen binding protein can also include HCDR1-3 and H-FR1-4, the HCDR1 can include an amino acid sequence as shown in SEQ ID NO: 18, the HCDR2 can include an amino acid sequence as shown in SEQ ID NO: 19, the HCDR3 can include an amino acid sequence as shown in SEQ ID NO: 20, the H-FR1 can include an amino acid sequence as shown in SEQ ID NO: 33, the H-FR2 can include an amino acid sequence as shown in SEQ ID NO: 35, the H-FR3 can include an amino acid sequence as shown in SEQ ID NO: 38, and the H-FR4 can include an amino acid sequence as shown in SEQ ID NO: 40; the antigen binding protein can also include VH and CH, the VH can include an amino acid sequence as shown in SEQ ID NO: 46, and the CH can include an amino acid sequence as shown in SEQ ID NO: 48; and the antigen binding protein can also include a light chain and a heavy chain, the light chain can include an amino acid sequence as shown in SEQ ID NO: 53, and the heavy chain can include an amino acid sequence as shown in SEQ ID NO: 54. For example, the antigen binding protein can include an antibody light chain and a heavy chain the same as those of 16H46L39am.

Reference Antibody

The antigen binding protein provided in this application can compete with a reference antibody for binding to C5.

In the present application, the reference antibody can include LCDR1-3, the LCDR1 can include an amino acid sequence as shown in SEQ ID NO: 69, the LCDR2 can include an amino acid sequence as shown in SEQ ID NO: 16, and the LCDR3 can include an amino acid sequence as shown in SEQ ID NO: 17. In some cases, the antigen binding protein of the present application can include LCDR1-3, the LCDR1 can include an amino acid sequence as shown in any one of SEQ ID NOs: 1-15, the LCDR2 can include an amino acid sequence as shown in SEQ ID NO: 16, and the LCDR3 can include an amino acid sequence as shown in SEQ ID NO: 17.

In the present application, the reference antibody can include HCDR1-3, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

In the present application, the reference antibody can include LCDR1-3 and HCDR1-3, the LCDR1 can include an amino acid sequence as shown in SEQ ID NO: 69, the LCDR2 can include an amino acid sequence as shown in SEQ ID NO: 16, the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20. In some cases, the antigen binding protein of the present application can include LCDR1-3 and HCDR1-3, the LCDR1 can include an amino acid sequence as shown in any one of SEQ ID NOs: 1-15, the LCDR2 can include an amino acid sequence as shown in SEQ ID NO: 16, the LCDR3 can include an amino acid sequence as shown in SEQ ID NO: 17, the HCDR1 can include an amino acid sequence as shown in SEQ ID NO: 18, the HCDR2 can include an amino acid sequence as shown in SEQ ID NO: 19, and the HCDR3 can include an amino acid sequence as shown in SEQ ID NO: 20.

In the present application, the reference antibody can include a light chain variable region VL and a heavy chain variable region VH, the VL can include an amino acid sequence as shown in any one of SEQ ID NOs: 41-43, and the VH can include an amino acid sequence as shown in any one of SEQ ID NOs: 44-46.

Immunoconjugate

In another aspect, the present application further provides an immunoconjugate. In the present application, the isolated antigen binding protein can be crosslinked with other compounds, such as therapeutic agents, to form the immunoconjugate, such as antibody-drug conjugates (ADCs). Suitable therapeutic agents include cytotoxins, alkylating agents, DNA minor groove binding molecules, DNA intercalators, DNA crosslinking agents, histone deacetylase inhibitors, nuclear export inhibitors, proteasome inhibitors, inhibitors of topoisomerase I or II, heat shock protein inhibitors, tyrosine kinase inhibitors, antibiotics, and anti-mitotic agents, e.g., SN-38. In ADCs, antibodies are cross-linked with therapeutic agents through linkers which are cleavable, e.g., peptide linkers, disulfide linkers or hydra-zone linkers. For example, linkers may be peptide linkers, e.g., Val-Cit, Ala-Val, Val-Ala-Val, Lys-Lys, Pro-Val-Gly-Val-Val (SEQ ID NO: 71), Ala-Asn-Val, Val-Leu-Lys, Ala-Ala-Asn, Cit-Cit, Val-Lys, Lys, Cit, Ser, or Glu. ADCs can be prepared as described in U.S. Pat. Nos. 7,087,600; 6,989,452; and 7,129,261; PCT Publications WO 02/096910; WO 07/038,658; WO 07/051,081; WO 07/059, 404; WO 08/083,312; and WO 08/103,693; U.S. Patent Publications 20060024317; 20060004081; and 20060247295.

Nucleic Acid

In another aspect, the present application further provides an isolated nucleic acid molecule, which can encode the isolated antigen binding protein of the present application. The isolated nucleic acid molecule of the present application can be isolated nucleotides, deoxyribonucleotides or ribo-nucleotides of any length, or analogues thereof isolated from its natural environment or synthesized artificially, which can encode the isolated antigen binding protein of the present application.

Vector

In another aspect, the present application further provides a vector, which can include the nucleic acid molecule of the present application. The vector can make the genetic ele-ments it carries be expressed in a host cell by transforming, transducing, or transfecting the host cell. For example, the vector can include: plasmid; phagemid; Cosmid; artificial chromosomes, such as yeast artificial chromosomes (YACs), bacterial artificial chromosomes (BACs) or P1-derived arti-ficial chromosomes (PACs); phages, such as lambda phages or M13 phages and animal viruses, and the like. The species of animal viruses used as the vector are retrovirus (including lentivirus), adenovirus, adeno-associated virus, herpes virus (e.g., herpes simplex virus), poxvirus, baculovirus, papil-loma virus, papovavirus (e.g., SV40). Further for example, the vector may contain various elements for controlling the expression, including promoter sequences, transcription ini-tiation sequences, enhancer sequences, selective elements and reporter genes. In addition, the vector may also contain replication initiation sites. Moreover, the vector may also include ingredients that help its entry into cells, such as virion, lipidosome or protein coat, but not only these sub-stances.

Cell

In another aspect, the present application further provides a cell, which can include the nucleic acid molecule of the present application or the vector of the present application. The cell can include the offspring of a single cell. Due to natural, accidental or intentional mutations, the offspring may not necessarily be exactly the same as the original parent cell (in the form of the total DNA complement or in the genome).

For example, the cell can include prokaryotic cells, yeast cells or higher eukaryotic cells. Prokaryotes suitable for this purpose include gram-negative and gram-positive bacteria, e.g., enterobacteria such as *Escherichia coli, Enterobacter, Erwinia, Klebsiella, Proteus, Salmonella, Serratia*, and *Shigella*, as well as Bacilli, *Pseudomonas* and *Streptomyces*.

For example, eukaryotic microorganisms such as filamen-tous fungi or yeast may also be used as suitable cloning or expression hosts for the vector of the present application. Among lower eukaryotic host microorganisms, the most commonly used is *Saccharomyces cerevisiae*. A variety of other genera, species, and strains are also commonly avail-able and can be used in the present application, e.g., *Schi-zosaccharomyces pombe, Kluyveromyces, Candida, Tricho-derma, Neurospora crassa*, and filamentous fungus, e.g., *Neurospora, Penicillium, Tolypocladium* and *aspergillus* host cells, e.g., *A. nidulans* and *A. niger*.

For example, vertebrate cells and vertebrate cells propa-gated in culture (tissue culture) are suitable cloning or expression hosts for the vector of the present application.

For example, the cells can include mammal host cell lines, for example, monkey kidney cells, human embryonic kidney cell lines, young hamster kidney cells, Chinese hamster ovary cells, mouse sertoli cells, human cervical cancer HeLa cells (HELA), canine kidney cells, human lung cells, human liver cells, mouse breast cancer cells or NSO cells.

For example, the cells can also include cells transfected with the vector of the present application in vitro. For example, the cells can be bacterial cells (e.g., *E. coli*), yeast cells, or eukaryotic cells, such as COS cells, Chinese Ham-ster Ovary (CHO) cells, CHO-K1 cells, LNCAP cells, HeLa cells, HEK293 cells, COS-1 cells, NSO cells or myeloma cells. In some embodiments, the cells can be mammal cells. For example, the mammal cells can be HEK293 cells.

Preparation

In another aspect, the present application further provides a method for preparing the isolated antigen binding protein of the present application, which can include culturing the cell of the present application under conditions allowing the expression of the isolated antigen binding protein of the present application.

Prevention, Alleviation and/or Treatment

In another aspect, the present application further provides use of the isolated antigen binding protein, the nucleic acid molecule, the vector, the cell, and/or the pharmaceutical composition in the preparation of a medicament for prevent-ing, alleviating and/or treating a C5-related disease or dis-order.

In another aspect, the present application further provides a method for preventing, alleviating or treating a C5-related disease or disorder, which can include administering to a subject in need thereof the isolated antigen binding protein, the nucleic acid molecule, the vector, the cell, and/or the pharmaceutical composition of the present application.

For example, the administration can be carried out in various ways, such as intravenous, intraperitoneal, subcuta-neous, intramuscular, topical or intradermal administration.

In another aspect, the present application further provides the isolated antigen binding protein, the nucleic acid mol-ecule, the vector, the cell, and/or the pharmaceutical com-position, which can be used for preventing, alleviating, or treating a C5-related disease or disorder.

For example, the subject can include human and non-human animals. For example, the subject can include, but not limited to, cat, dog, horse, pig, cow, goat, rabbit, mouse, rat, or monkey.

Pharmaceutical Composition

In another aspect, the present application further provides a pharmaceutical composition, which includes the isolated antigen binding protein of the present application, the nucleic acid molecule of the present application, the vector of the present application and/or the cell of the present application, and optionally a pharmaceutically acceptable adjuvant.

For example, the pharmaceutical composition can additionally contain one or more other therapeutic agents suitable for treating or preventing the C5-related disease or disorder.

For example, the pharmaceutically acceptable adjuvant enhances or stabilizes the composition, or promotes the preparation of the composition. For example, the pharmaceutically acceptable adjuvant can include physiologically compatible solvents, dispersion media, coatings, antibacterial and antifungal agents, isotonic agents, and absorption delaying agents, etc.

For example, the pharmaceutical composition can be administered by a variety of methods known in the art, depending on the desired result, route of administration and/or mode of administration. For example, the administration can be intravenous, intramuscular, intraperitoneal, or subcutaneous administration, or administration near the target site. For example, the pharmaceutical composition is formulated so that they can be intravitreally administered into eyes. For example, depending on the route of administration, the isolated antigen binding protein (e.g., antibodies, bispecific and multi-specific molecules) can be coated with materials to protect the compound against the action of acids or other natural conditions, which can inactivate the compound.

For example, the pharmaceutical composition can be sterile and fluid. For example, proper fluidity can be maintained by using coating materials such as lecithin, or by maintaining the required particle size in the case of dispersion, and by using surfactants.

For example, isotonic agents, for example, saccharides and polyols, such as mannitol, sorbitol or sodium chloride, are included in the composition. For example, the prolonged absorption of the injectable pharmaceutical composition can be realized by including in the pharmaceutical composition an agent which delays absorption, for example, aluminum monostearate or gelatin.

For example, the isolated antigen binding protein, the nucleic acid molecule, the vector and/or the cell are prepared in admixture with optional pharmaceutically acceptable carriers, excipients, or stabilizers for storage. For example, the pharmaceutical composition can be in a form of freeze-dried preparation or aqueous solution.

For example, the pharmaceutically acceptable adjuvant can include pharmaceutically acceptable carriers, excipients, or stabilizers.

For example, the acceptable carriers, excipients, or stabilizers are non-toxic to the recipient at the dosage and concentration used, and buffering agents, such as phosphate, citrate, acetate, and other organic acids, are included.

For example, the pharmaceutical composition comprising the isolated antigen binding protein of the present application can be water-soluble.

For example, the pharmaceutical composition for in vivo administration can be sterile. This can be easily achieved by filtration through sterile filtration membrane or other methods. For example, administration of the pharmaceutical composition comprising the isolated antigen binding protein of the present application in the form of sterile aqueous solution can be conducted in a variety of ways, including, but not limited to, oral, subcutaneous, intravenous, intranasal, intra-aural, transdermal, topical (e.g., gel, ointment, lotion, cream, etc.), intraperitoneal, intramuscular, intrapulmonary, parenteral, rectal, or intraocular administration. In some cases, for example, in the treatment of wounds and inflammation, the isolated antigen binding protein can be directly applied as a solution or spray.

For example, the pharmaceutical composition can be prepared in accordance with the methods well known and conventionally practiced in the art. For example, the pharmaceutical composition can be prepared under GMP conditions. In general, a therapeutically effective dose or an effective dose of C5 binding protein is used in the pharmaceutical composition of the present application. For example, C5 binding protein can be formulated into pharmaceutically acceptable dosage forms by conventional methods known to those skilled in the art. Dosage regimens are adjusted to provide an optimal desired response (e.g., a therapeutic response). The actual dosage level of the active ingredient in the pharmaceutical composition of the present application can be varied in order to obtain an amount of the active ingredient effective to achieve the desired therapeutic response, composition and mode of administration for a particular patient without being toxic to the patient. The dose level selected depends on a variety of pharmacokinetic factors, such as the activity of the particular composition or ester, salt or amide thereof used in this application, the route of administration, the time of administration, the excretion rate of the particular compound being used, the duration of treatment, other drugs, compounds and/or substances used in combination with the particular composition used, the age, sex, weight, status, general health and prior medical history of the subject being treated, as well as other factors.

For example, subcutaneous administration can be used in situations where the patients can administer the pharmaceutical composition themselves. Many protein therapeutics are not effective enough to allow the formulation of a therapeutically effective dose of the maximum acceptable volume to be administered subcutaneously. The antigen binding protein disclosed in the present application can be suitable for subcutaneous administration, for example, for increased potency, improved plasma half-life, and improved solubility.

As known in the art, protein therapeutics can be delivered through intravenous infusion or bolus injection. The antigen binding protein disclosed in the present application can also be delivered through such methods.

Detection Method

In another aspect, the present application further provides a method for detecting C5 in a sample, which includes administering the isolated antigen binding protein of the present application.

For example, a sample obtained from the subject is contacted with the isolated antigen binding protein of the present application (e.g., C5 binding protein). For example, the C5 binding protein is labeled with a detectable label or a reporter molecule or an anti-C5 binding protein is used as a capture ligand to selectively isolate C5 from the sample of the patient. Alternatively, unlabeled anti-C5 binding protein can bind to a second antibody for use in the detection application, where the second antibody itself carries a detectable label. The detectable label or reporter molecule can be a radioisotope such as 3H, 14C, 32P, 35S or 125I; and it can also be a fluorescent or chemiluminescent moiety such as fluorescein isothiocyanate, rhodamine; or an enzyme such as alkaline phosphatase, beta-galactosidase, horseradish peroxidase, or luciferase. Specific exemplary assays that can be used to detect or measure C5 in a sample include enzyme-linked immunosorbent assay (ELISA), radioimmunoassay (RIA), and fluorescence-activated cell sorting (FACS).

Samples that can be used in the C5 detection of the present application can include any tissue or fluid sample obtained from a subject in a normal or pathological condition that contains detectable amounts of C5 protein or fragments thereof. For example, The level of C5 protein measured in a particular sample obtained from a healthy subject (e.g., a subject not suffering from a C5-related disease) can be used to initially establish a baseline or standard level of C5. This baseline level of C5 is then compared to C5 levels measured in samples obtained from individuals suspected of having a C5-related disease or disorder or symptoms associated with the disorder.

C5 binding protein may contain no additional labels or may contain N-terminal or C-terminal labels. For example, the label is biotin. In binding assays, the position of labels (if any) allows to determine the orientation of the peptide relative to the surface on which the peptide is bound. For example, if the surface is coated with avidin, the peptide containing an N-terminal biotin will keep the C-terminal portion of the peptide away from the surface.

Without intending to be limited by any theory, the following examples are only intended to illustrate the isolated antigen binding protein, preparation method and use of the present application, and are not intended to limit the inventive scope of the present application.

EXAMPLES

TABLE 1

| Amino acid sequence listing of antigen binding proteins | | | | | | |
|---|---|---|---|---|---|---|
| Antigen binding protein | CHI-16 | 16H1L2m | 16H46L39am | ECU | RAV | SKY59 |
| Light chain | SEQ ID NO: 49 | SEQ ID NO: 51 | SEQ ID NO: 53 | SEQ ID NO: 55 | SEQ ID NO: 55 | SEQ ID NO: 58 |
| Heavy chain | SEQ ID NO: 50 | SEQ ID NO: 52 | SEQ ID NO: 54 | SEQ ID NO: 56 | SEQ ID NO: 57 | SEQ ID NO: 59 |
| Light chain CDR1 | SEQ ID NO: 1 | SEQ ID NO: 2 | SEQ ID NO: 2 | | | |
| Light chain CDR2 | SEQ ID NO: 16 | SEQ ID NO: 16 | SEQ ID NO: 16 | | | |
| Light chain CDR3 | SEQ ID NO: 17 | SEQ ID NO: 17 | SEQ ID NO: 17 | | | |
| Light chain FR1 | SEQ ID NO: 21 | SEQ ID NO: 22 | SEQ ID NO: 23 | | | |
| Light chain FR2 | SEQ ID NO: 24 | SEQ ID NO: 24 | SEQ ID NO: 25 | | | |
| Light chain FR3 | SEQ ID NO: 26 | SEQ ID NO: 27 | SEQ ID NO: 28 | | | |
| Light chain FR4 | SEQ ID NO: 29 | SEQ ID NO: 30 | SEQ ID NO: 30 | | | |
| Light chain variable region | SEQ ID NO: 41 | SEQ ID NO: 42 | SEQ ID NO: 43 | | | |
| Light chain constant region | SEQ ID NO: 47 | SEQ ID NO: 47 | SEQ ID NO: 47 | | | |
| Heavy chain CDR1 | SEQ ID NO: 18 | SEQ ID NO: 18 | SEQ ID NO: 18 | | | |
| Heavy chain CDR2 | SEQ ID NO: 19 | SEQ ID NO: 19 | SEQ ID NO: 19 | | | |
| Heavy chain CDR3 | SEQ ID NO: 20 | SEQ ID NO: 20 | SEQ ID NO: 20 | | | |
| Heavy chain FR1 | SEQ ID NO: 31 | SEQ ID NO: 32 | SEQ ID NO: 33 | | | |
| Heavy chain FR2 | SEQ ID NO: 34 | SEQ ID NO: 35 | SEQ ID NO: 35 | | | |
| Heavy chain FR3 | SEQ ID NO: 36 | SEQ ID NO: 37 | SEQ ID NO: 38 | | | |
| Heavy chain FR4 | SEQ ID NO: 39 | SEQ ID NO: 40 | SEQ ID NO: 40 | | | |
| Heavy chain variable region | SEQ ID NO: 44 | SEQ ID NO: 45 | SEQ ID NO: 46 | | | |
| Heavy chain constant region | SEQ ID NO: 48 | SEQ ID NO: 48 | SEQ ID NO: 48 | | | |

TABLE 2

| Nucleotide sequence listing of antigen binding proteins | | |
|---|---|---|
| Antigen binding protein | 16H1L2m | 16H46L39am |
| Heavy chain variable region | SEQ ID NO: 61 | SEQ ID NO: 62 |
| Light chain variable region | SEQ ID NO: 63 | SEQ ID NO: 64 |
| Light chain | SEQ ID NO: 65 | SEQ ID NO: 67 |
| Heavy chain | SEQ ID NO: 66 | SEQ ID NO: 68 |

Example 1 Anti-Human C5 Mouse Monoclonal Antibody

1) Determination of Binding to Human C5 Antigen by ELISA

The binding of culture supernatants of 9 hybridoma cell lines expressing high-affinity mouse monoclonal antibodies to human C5 antigen was determined by ELISA. The ELISA plate was coated with human C5 (as shown in SEQ ID NO: 60) at 4° C. overnight. The coating solution was discarded. The wells were blocked with bovine serum albumin (BSA) dissolved in a phosphate-buffered saline (PBS) for 1 hr., and washed with a PBST solution (a PBS solution containing 0.02% Tween). Then, 100 ng/mL and 20 ng/mL of culture supernatants of mouse monoclonal antibody hybridoma cell line and eculizumab (ECU) as positive controls were added, respectively. The well plate was incubated at room temperature for 1 hr. The wells were washed with a PBST solution, and an RP-labeled detection antibody was added to detect the binding capacity of each antibody.

Among others, the m16 mouse antibodies were selected for use in the subsequent antibody preparation.

Example 2 Anti-Human C5 Chimeric Antibody

1) Cloning of Heavy and Light Chain Variable Region Genes of Anti-Human C5 Mouse Monoclonal Antibody m16

The method of obtaining DNA fragments containing sequences encoding the heavy and light chain variable regions of the mouse antibody m16 involves isolating the mRNAs from the m16 mouse hybridoma cells to prepare cDNAs. The DNA fragments of the heavy chain variable region and light chain variable region were isolated from the cDNA by polymerase chain reaction (PCR). The recovered DNA fragments were cloned into a TOPO-TA vector (Yeasen) and subject to sequencing. The software Discovery Studio was used to predict and obtain the amino acid sequence (SEQ ID NO: 44) of the variable region (VH) encoding the m16 heavy chain and the amino acid sequences of its complementary determining region, HCDR1 (SEQ ID NO: 18), HCDR2 (SEQ ID NO: 19), and HCDR3 (SEQ ID NO: 20), as well as the amino acid sequence of the light chain variable region (VL) (SEQ ID NO: 41) and the amino acid sequences of its complementary determining region, LCDR1 (SEQ ID NO: 1), LCDR2 (SEQ ID NO: 16) and LCDR3 (SEQ ID NO: 17).

2) Preparation of Anti-Human C5 Chimeric Antibody

The gene sequences of mouse heavy chain variable region and light chain variable region were cloned from the mouse hybridoma cells. The human IgG1 constant region sequence (with an amino acid sequence as shown in SEQ ID NO: 48) which did not have an ADCC (antibody-dependent cell-mediated cytotoxicity) toxicity after the amino acid mutation was selected. The heavy chain variable region gene of the mouse antibody m16 was linked to the human IgG1 constant region gene to form a chimeric gene, and the light chain variable region gene was linked to the human Kappa light chain constant region sequence (with the amino acid sequence as shown in SEQ ID NO: 47) to form a chimeric gene, which were subsequently inserted into the vector pcDNA3.1 (Biofeng Lab). Finally, a chimeric antibody molecule was expressed in the expression system of the human renal epithelial cells (293) (purchased from Thermo fisher, Item No.: XP293) to give the chimeric antibody CHI-16. Eculizumab (ECU, with a light chain amino acid sequence of SEQ ID NO: 55 and a heavy chain amino acid sequence of SEQ ID NO: 56), Ravulizumab (RAV, with a light chain amino acid sequence of SEQ ID NO: 55 and a heavy chain amino acid sequence of SEQ ID NO: 57), SKY59 (with a light chain amino acid sequence of SEQ ID NO: 58 and a heavy chain amino acid sequence of SEQ ID NO: 59) were taken as positive control antibodies.

3) Determination of Binding of Chimeric Antibody to Human C5 Antigen by ELISA The ELISA plates (purchased from Costar, Item No.: 42592) were coated with antibodies Eculizumab (ECU), Ravulizumab (RAV), SKY59, and CHI-16 at 4° C. overnight. The coating solution was discarded. The wells were blocked with 2.5% skimmed milk dissolved in a phosphate-buffered saline (PBS) for 1 hour, and washed with a PBST solution (a PBS solution containing 0.02% Tween). Then, 100 μL of human C5 gradient diluent was added into each well and incubated at 37° C. for 1 hr., respectively. The wells were washed with PBST. Finally, 100 μL of HRP-labelled anti-histidine antibody (purchased from Sino Biological, Item No.: 105327-MM02T-H) was added as the detection antibody into each well. The results are shown in FIG. 1. The stronger the binding of the antibody to human C5, the darker the color at the same concentration of the human C5 antibody, and the higher the OD450. It can be seen from FIG. 1 that the binding activity of the chimeric antibody CHI-16 to human C5 is better than that of ECU and Ravulizumab (RAV).

4) Inhibitory Effect of Chimeric Antibody on Complement-Mediated Hemolysis In Vitro The method of hemolysis inhibition experiment in vitro is as follows: sheep red blood cells (purchased from Bio-channel, Item No.: BC-RBC-S003) were washed three times with GVB++ buffer (containing Mg++ and Ca++, purchased from Tiandz, Item No.: 25-02080), and hemolysin (1:2000, rabbit-anti-sheep red blood cell antibody) (purchased from Beijing Bersee Science and Technology, Item No.: BM351Y) was added. The mixture was left at room temperature for 10 minutes to activate the sheep red blood cells. The activated sheep red blood cells were washed twice with GVB++ buffer, centrifuged and diluted with GVB++ buffer to 30 μL ($5\times10^6$ cells). 50 μL of 2.6% normal human serum (NHS, diluted with GVB++) (purchased from Stem Express, Item No.: PBSR015C) was mixed with 50 μL of antibody gradient diluent formulated with GVB++(initial concentration of the antibody dilution concentration was 2 μg/ml (final concentration), 2×dilution, 6 dilution gradients). The well plate (purchased from Costar, Item No.: 3799) was incubated at room temperature for about 30 minutes. At the same time, a control group of antibody-free samples was set, that is, a group to which only 1% NHS with the same volume as the above antibody mixture was added (complete hemolysis control group). 30 μL of the activated sheep red blood cells were added into the well plate in which the NHS and the antibodies had been incubated and incubated at room temperature for 1 hr. After centrifugation, the supernatant was collected and read by a plate reader at 405 nm for the absorbance. The inhibitory effect of the anti-C5 antibody on hemolysis was represented by the inhibition rate (%) calculated following the equation below: Inhibition Rate (%)=100×[(the OD reading of antibody-free sample–the OD background value of serum)–(the OD reading of antibody-containing sample–the OD background value of serum)]/(the OD reading of antibody-free sample–the OD background value of serum).

Figure 2:
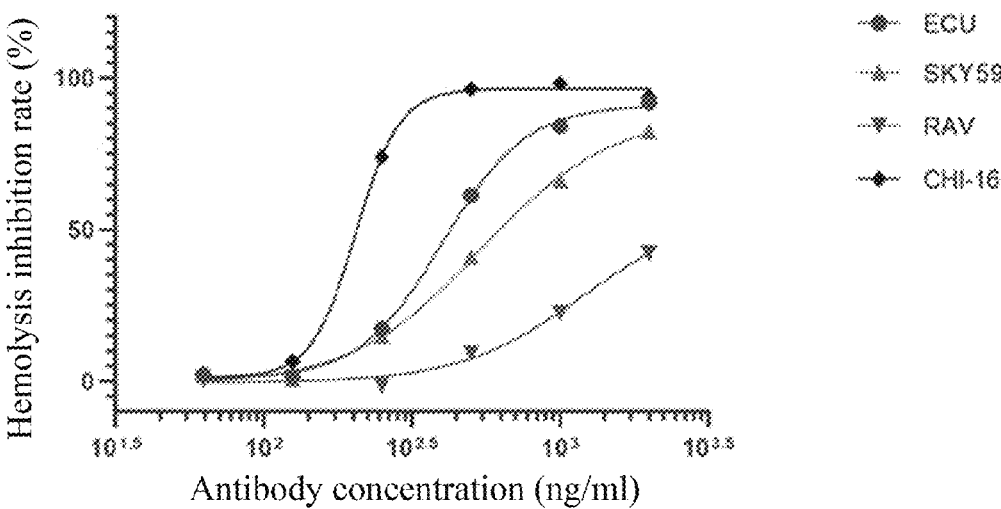
FIG. 2 shows the results of the hemolysis inhibition assay of the chimeric antibody of this application and the positive control antibody.

The results are shown in FIG. 2. The NHS with a final concentration of 1% can lead to the hemolysis of the activated sheep red blood cells; the addition of antibodies can inhibit the hemolysis; and the inhibitory effect of CHI-16 is better than that of the positive control antibodies, Eculizumab (ECU), Ravulizumab (RAV), and SKY59. $IC_{50}$ can be used to evaluate the concentration of each antibody at 50% inhibition of hemolysis. The $IC_{50}$ of each group is shown in Table 3 below. The $IC_{50}$ of the chimeric antibody CHI-16 is lower than that of the positive control antibodies, Eculizumab (ECU), Ravulizumab (RAV), and SKY59, indicating better inhibitory effect of hemolysis in vitro.

TABLE 3

Inhibitory effect of chimeric antibody on hemolysis

|  | ECU | RAV | SKY59 | CHI-16 |
|---|---|---|---|---|
| $IC_{50}$ (ng/ml) | 401.3 | 1186 | 542.5 | 204.5 |

Example 3 Point Mutation Antibody with Antibody Isomerization Removed

1) Change in Production of Antibody with Single Point Mutation in Light Chain CDR1 Region As aspartic acid (D) and glycine (G) in the CDR regions are easy to deamination when linked, resulting in unstable binding between antigen and antibody, the 32D and 33G of light chain CDR1 region of the CHI-16 humanized antibody 16HDa was subject to single-point mutation of multiple amino acids to screen the mutated amino acid with the least influence on the antigen binding capacity and the production.

Figure 3:
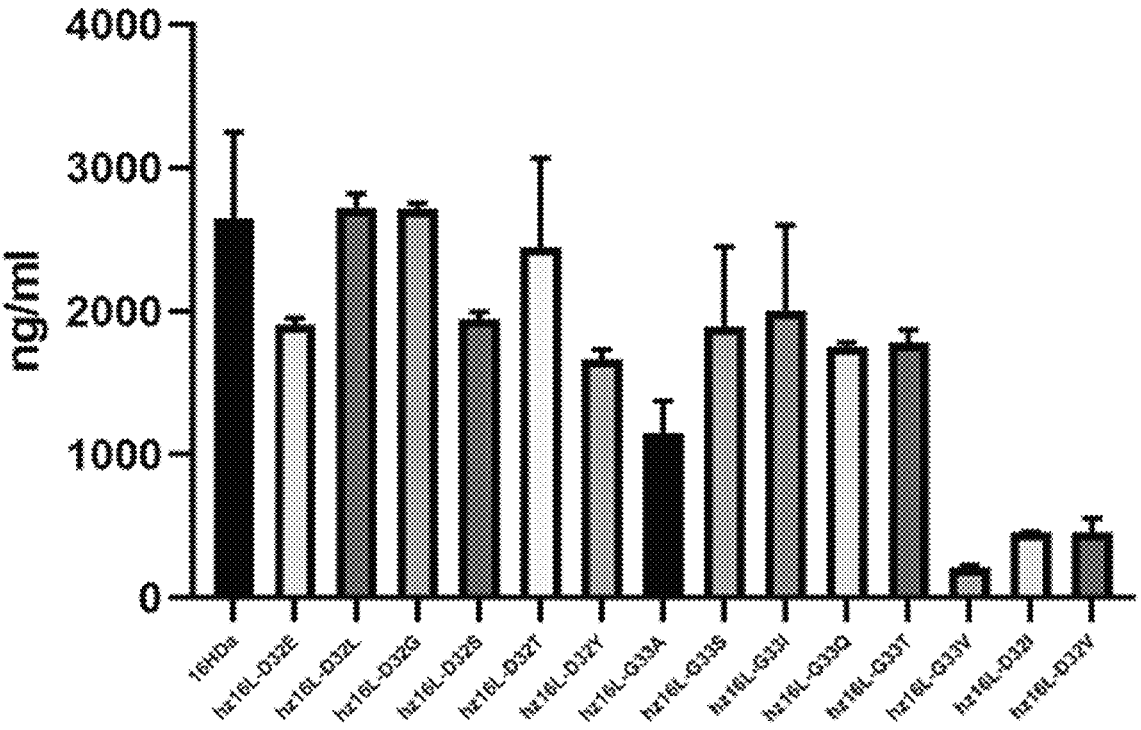
FIG. 3 shows the experimental results of changes in the yield of the humanized antibody of this application after site mutation.

For the 32D site in the 16HDa light chain variable region, vectors with single point mutation of D32E, D32I, D32L, D32G, D32S, D32T, D32V, and D32Y were constructed, respectively. For the 33G site in the 16HDa light chain variable region, vectors with single point mutation of G33A, G33S, G33I, G33Q, G33T, and G33V were constructed, respectively. Humanized antibody with single point mutation at D32 was produced in a 24-well plate using the 293 cells, and the unmutated humanized antibody 16HDa expressed under the same conditions was taken as control. The culture supernatant was collected for primary quantification by ELISA competition method to detect the production (Titer) of the mutant antibody and the control antibody. The method is as follows. The diluted supernatant to be tested was mixed with an equivalent volume of the HRP-labelled anti-human IgG as the detection antibody, added into an ELISA plate coated with 1 ug/ml of CHI-16, and then incubated at room temperature for 1 hr. At the same time, CHI-16 was used as standard to make a standard curve in accordance with the same method. The value was read after development. The Titer in the supernatant can be calculated in accordance with the standard curve. The results are shown in FIG. 3. Among those mutant antibodies, the production of D32L, D32G and D32T were not significantly changed as compared with that of the control antibody without mutation.

Figure 4:
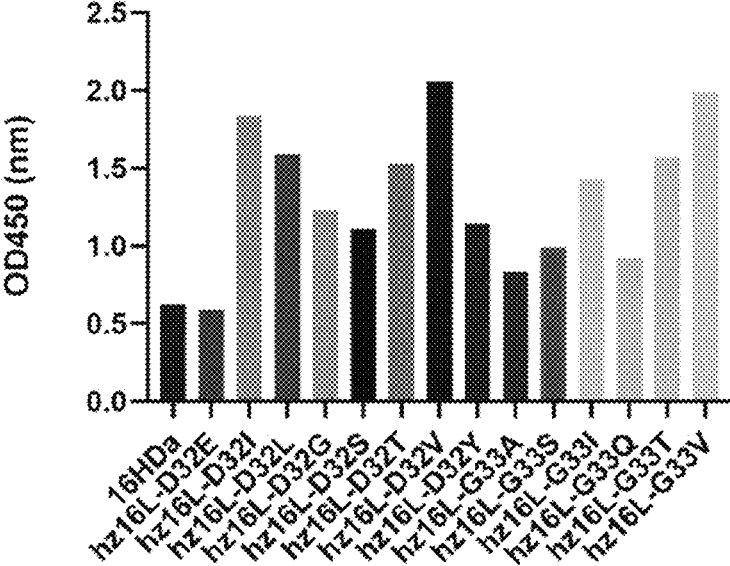
FIG. 4 shows the experimental results of changes in the antigen binding capacity of the humanized antibody of this application after site mutation.

2) Change in Antigen Binding Capacity of Antibody with Single Point Mutation in Light Chain CDR1 Region by ELISA Humanized antibodies with single point mutation at D32 and G33 were produced in a 24-well plate using the 293 cells, and the unmutated humanized antibody 16HDa expressed under the same conditions was taken as control. The culture supernatant was collected for detecting the binding capacity of the mutant antibody and the control antibody to the antigen by ELISA competition method. The method is as follows: The ELISA plate was coated with the control antibody and stood at 4° C. overnight. The coating solution was discarded. The wells were blocked with skimmed milk dissolved in a phosphate-buffered saline (PBS) for 1 hour, and washed with a PBST solution (a PBS solution containing 0.02% Tween). Then, a mixed solution of the mutant antibody with the C5 antigen (his tag) was added into each well, and incubated at room temperature for 1 hr. The wells were washed with PBST, and then the HRP-labelled anti-histidine antibody was added into each well as the detection antibody. The results are shown in FIG. 4. If the binding capacity of the antibody to the antigen decreases after mutation, the OD450 value will increase. Thus, among all the mutant antibodies, the antibody with D32E mutation can maintain the same antigen binding capacity as that of the antibody without mutation, and secondly a mutation resulting in similar antigen binding capacity is G33A. Based on the previous results of change in production, we selected to introduce the D32E mutation in the antibody light chain variable region into the subsequent humanized antibody so as to avoid a possible deamination reaction during the binding of antigen.

Example 4 Anti-Human C5 Humanized Antibody

1) Preparation of Anti-Human C5 Humanized Antibody

The chimeric antibody CHI-16 was humanized to finally give two different humanized antibodies: 16H1L2m and 16H46L39am. The nucleotide sequence of the 16H1L2m heavy chain is shown in SEQ ID NO: 66, the nucleotide sequence of the 16H1L2m light chain is shown in SEQ ID NO: 65, the nucleotide sequence of the 16H1L2m heavy chain variable region is shown in SEQ ID NO: 61, the nucleotide sequence of the 16H1L2m light chain variable region is shown in SEQ ID NO: 63. The nucleotide sequence of the 16H46L39am heavy chain is shown in SEQ ID NO: 68, the nucleotide sequence of the 16H46L39am light chain is SEQ ID NO: 67, the nucleotide sequence of the 16H46L39am heavy chain variable region is shown in SEQ ID NO: 62, and the nucleotide sequence of the 16H46L39am light chain variable region is shown in SEQ ID NO: 64.

The gene sequences of mouse heavy chain variable region and light chain variable region were cloned from the mouse hybridoma cells. The human IgG1 constant region gene sequence (SEQ ID NO: 48) which did not have an ADCC (antibody-dependent cell-mediated cytotoxicity) toxicity after the amino acid mutation was selected. The heavy chain variable region genes of the humanized antibodies 16H1L2m and 16H46L39am were linked to the human IgG1 constant region gene to form a chimeric gene, and the light chain variable region gene was linked to the human Kappa light chain constant region (as shown in SEQ ID NO: 47) to form a chimeric gene, which were subsequently inserted into the transient transfection expressing vector pcDNA3.1. 100 mL of the 293 cells were used to produce the humanized antibody protein by transient transfection to give the antibody proteins 16H1L2m and 16H46L39am. Eculizumab (ECU), Ravulizumab (RAV), SKY59, and the chimeric antibody CHI-16 produced under the same conditions were taken as positive control antibodies.

2) Inhibitory Effect of Humanized Antibody on Complement-Mediated In Vitro Hemolysis The inhibitory activity of anti-human C5 humanized antibody on complement activation in classical pathway (CP) and alternative pathway (AP) was detected by in vitro hemolysis inhibition test.

The method of in vitro hemolysis inhibition experiment in classical pathway (CP) are as shown in step 4) of Example 2. The inhibitory effect of the humanized antibodies 16H1L2m and 16H46L39am on complement-mediated in vitro hemolysis was detected in accordance with the method of step 4) of Example 2, wherein the gradient concentration diluent of the antibodies 16H1L2m and 16H46L39am formulated with GVB++(initial concentration of the antibody dilution concentration was 2 µg/ml (final concentration), 2× dilution, and 6 dilution gradients) were used.

Figure 5:
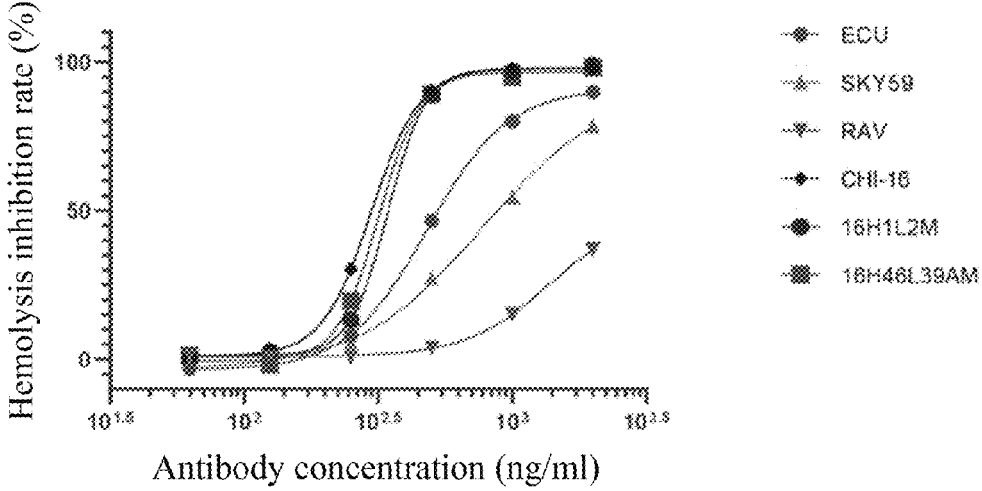
FIG. 5 shows the results of the classical pathway (CP) hemolysis inhibition assay of the humanized antibody of this application and the positive control antibody.

The experimental results are shown in FIG. 5. 16H1L2m and 16H46L39am have similar inhibitory effect with the chimeric antibody CHI-16, both better than those of the control groups Eculizumab (ECU), Ravulizumab (RAV), and SKY59. $IC_{50}$ and $IC_{90}$ represent the concentrations of each antibody at hemolysis inhibition rates of 50% and 90%, respectively.

The $IC_{50}$ and $IC_{90}$ values of each group are shown in Table 4:

TABLE 4

Inhibitory effect of anti-human C5 candidate humanized antibodies on hemolysis

|  | ECU | RAV | SKY59 | CHI-16 | 16H1L2m | 16H46L39am |
|---|---|---|---|---|---|---|
| $IC_{50}$ (ng/ml) | 558.80 | 2681.00 | 918.70 | 301.60 | 346.70 | 329.70 |
| $IC_{90}$ (ng/ml) | 1342.42 | 9062.67 | 3036.32 | 499.80 | 510.59 | 507.17 |

The method of in vitro hemolysis inhibition experiment in alternative pathway (AP) is as follows: normal rabbit red blood cells (purchased from Bio-channel, Item No.: BC-RBC-RAB003) were mixed with EGTA to inhibit the complement activated classic pathway. Normal human serum (NHS) treated by addition of GVB Mg+ EGTA (Tiandz/25-02090) and with a final concentration of 5% were incubated in well plates incubated with gradient diluents of various antibodies (initial concentration of antibodies (final concentration) was 200 µg/ml, 4×dilution, 6 gradients, the number of rabbit red blood cells is $5×10^6$, and washed three times with GVB Mg+ EGTA before addition) for incubation at room temperature for 1 hr. After centrifugation, the supernatant was collected and read at 405 nm for the absorbance. The inhibitory effect of the anti-C5 antibody on hemolysis was represented by the inhibition rate (%) calculated following the equation below: Inhibition Rate (%)=100×[(the OD reading of antibody-free sample−the OD background value of serum)−(the OD reading of antibody-containing sample−the OD background value of serum)]/(the OD reading of antibody-free sample−the OD background value of serum).

Figure 6:
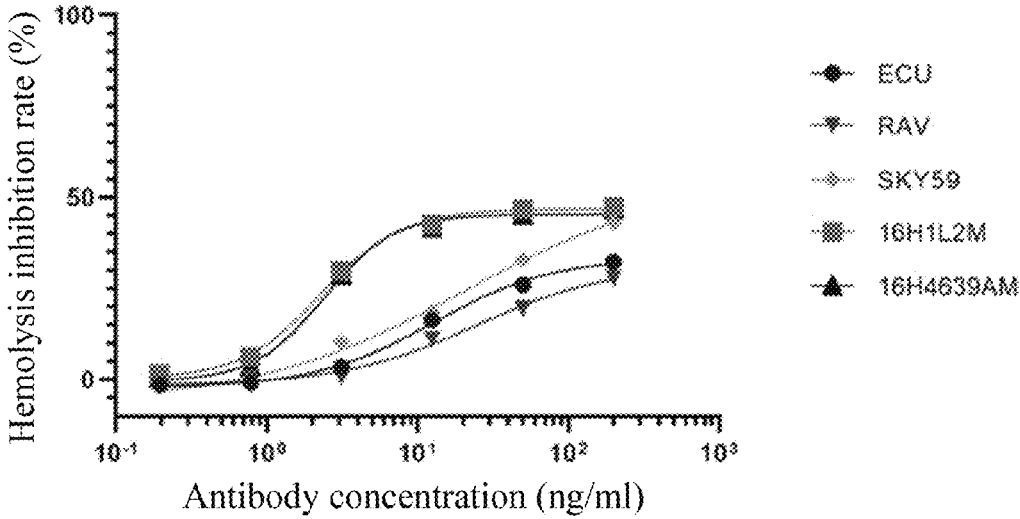
FIG. 6 shows the results of the alternative pathway (AP) hemolysis inhibition assay of the humanized antibody of this application and the positive control antibody.

The results are shown in FIG. 6. The inhibitory effects of 16H1L2m and 16H46L39am expressed in the 293 cells on hemolysis in alternative pathway are better than the biological activity of the three positive control antibodies Eculizumab (ECU), Ravulizumab (RAV), and SKY59.

3) Determination of Thermal Stability of Humanized Antibody by ELISA

Figure 7:
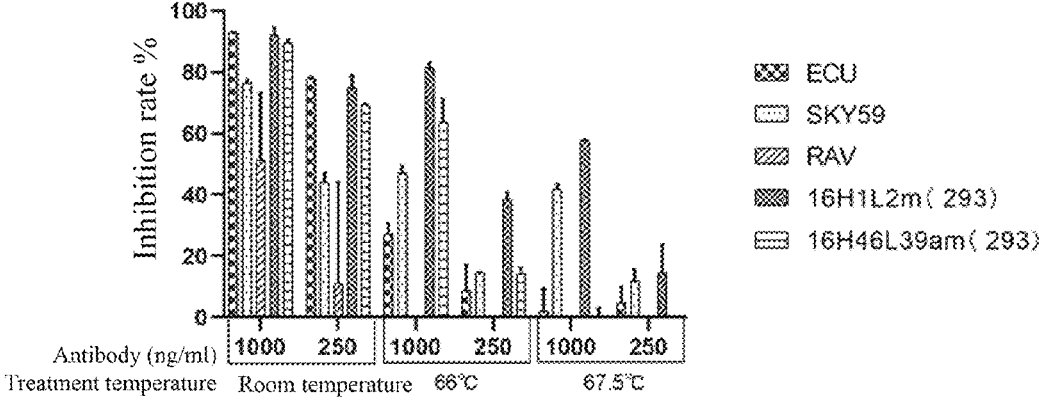
FIG. 7 shows the results of the thermal stability experiment of the humanized antibody of this application and the positive control antibody.

The ELISA plate (purchased from Corning, Item No.: 42592) was coated with the chimeric antibody CHI-16 at 4° C. overnight. The coating solution was discarded. The wells were blocked with 2.5% skimmed milk dissolved in a phosphate-buffered saline (PBS) for 1 hour, and washed with a PBST solution (a PBS solution containing 20% Tween). The antibodies to be tested were divided into three groups, and the respective groups were treated at the temperatures of room temperature (37° C.), 66° C., and 67.5° C. for 1 hr., respectively. The antibodies treated at different temperatures were diluted to 2000 ng/ml, 500 ng/ml, mixed with an equivalent volume of 500 ng/ml of the human C5 antigen, and added as the primary antibody into the wells for incubation at room temperature for 1 hr. The wells were washed with PBST, and then 100 µL of the HRP-labelled anti-histidine antibody (purchased from Sino Biological, Item No.: 105327-MM02T-H) was added into each well as the detection antibody. The antibodies were deactivated at high temperature, and incapable of binding to the human C5 antigen. The excess of the human C5 antigen would bind to the coated CHI-16 to development. Thus, the thermal stability of the antibodies could be evaluated. The better the thermal stability of the antibody, the lower the OD450 value, the stronger the ability of inhibiting the human C5 antigen binding. The results are shown in FIG. 7. The thermal stability of 16H1L2m and 16H46L39am are better than that of the control antibody.

4) Determination of Binding of Humanized Antibody to Human C5 Antigen by ELISA

The ELISA plates (purchased from Corning, Item No.: 42592) were coated with various antibodies (16H1L2m, 16H46L39am, ECU and RAV) at 4° C. overnight. The coating solution was discarded. The wells were blocked with 2.5% skimmed milk dissolved in a phosphate-buffered saline (PBS) for 1 hour, and washed with a PBST solution (a PBS solution containing 0.02% Tween). Then, 100 µL of the human C5 (his-tag) gradient diluent (the C5 was diluted to 1 µg/ml, followed by 3×dilution to give 7 gradients, with 100 µL/well) was added into each well, and incubated at room temperature for 1 hr. The wells were washed with PBST, and then 100 µL of HRP-labelled anti-histidine antibody (purchased from Sino Biological, Item No.: 105327-MM02T-H) was added at a ratio of 1:8000 into each well as the detection antibody.

Figure 8:
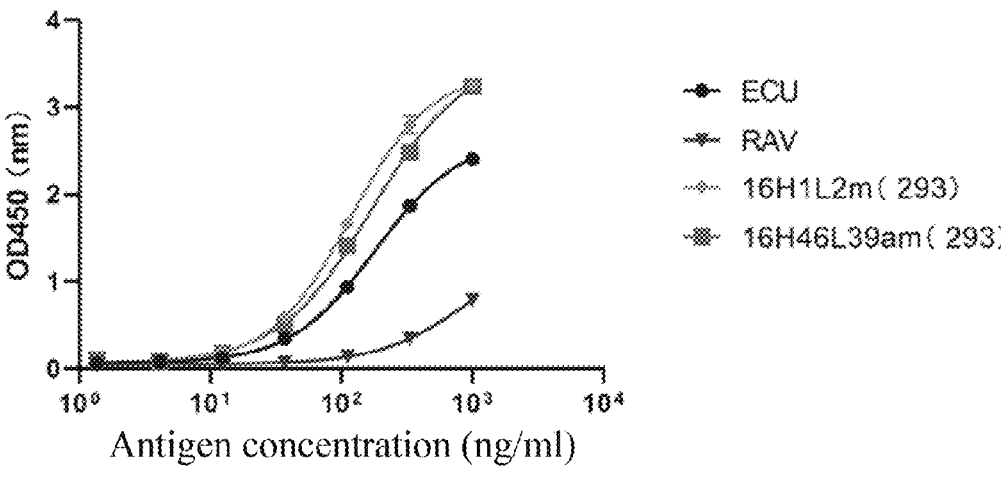
FIG. 8 shows the results of the binding assay between the humanized antibody of this application and the human C5 antigen.

The results are shown in FIG. 8. The stronger the binding of the antibody to the human C5, the darker the color at the same concentration of C5, the higher the OD450 value. $EC_{50}$ can be used to evaluate the concentration of antigen at the 50% binding capacity of various antibodies to the antigen. The lower $EC_{50}$ indicates the stronger binding capacity of the antibody to the human C5 antigen. The results are shown in FIG. 8. The binding capacities of 16H1L2m and 16H46L39am to antigen are both stronger than those of ECU and RAV. $EC_{50}$ values are shown in Table 5.

TABLE 5

| Binding capacity of anti-human C5 candidate humanized antibodies to antigen | | | | |
|---|---|---|---|---|
| | ECU | RAV | 16H1L2m | 16H46L39am |
| EC$_{50}$ (ng/ml) | 180.9 | 941.9 | 117.5 | 168.8 |

5) Affinity Assay of Humanized Antibodies

The binding affinity constants of the control antibody ECU and the humanized antibodies 16H1L2m and 16H46L39am to the antigen were determined with a molecular interaction analyzer (ForteBio Octet) by biological membrane interference technique (BLI). The dynamic fitting curve of affinity assay and the measurement of dynamic parameters in various channels were analyzed to calculate the affinity constants of various candidate humanized antibodies and ECU (see Table 6).

TABLE 6

| Affinity of anti-human C5 candidate humanized antibody and ECU binding to human C5 (Octet) | | | |
|---|---|---|---|
| | $K_D$ (M) | $K_a$ (1/Ms) | $K_d$ (1/s) |
| ECU | $3.02 \times 10^{-10}$ | $2.16 \times 10^5$ | $6.52 \times 10^{-5}$ |
| 16H1L2m | $3.59 \times 10^{-10}$ | $2.17 \times 10^5$ | $7.81 \times 10^{-5}$ |
| 16H46L39am | $3.69 \times 10^{-10}$ | $2.13 \times 10^5$ | $7.86 \times 10^{-5}$ |

In Table 6, $K_a$: association rate constant; $K_d$: dissociation rate constant; $K_D$: affinity constant, equal to $K_d/K_a$.

The results show that the affinity of 16H1L2m and 16H46L39am binding to the human C5 is similar to that of the control antibody ECU.

What is claimed is:

1. An isolated antigen binding protein, which is capable of binding to a complement factor 5 (C5) protein, comprising three complementary determining regions of a heavy chain variable region (VH): HCDR1, HCDR2, and HCDR3, and three complementary determining regions a light chain variable region (VL): LCDR1, LCDR2, and LCDR3, wherein the HCDR1 comprises the amino acid sequence of SEQ ID NO: 18, the HCDR2 comprises the amino acid sequence of SEQ ID NO: 19, the HCDR3 comprises the amino acid sequence of SEQ ID NO: 20, the LCDR1 comprises the amino acid sequence of SEQ ID NO: 1 or SEQ ID NO: 2, the LCDR2 comprises the amino acid sequence of SEQ ID NO: 16, and the LCDR3 comprises the amino acid sequence of SEQ ID NO:17.

2. The isolated antigen binding protein according to claim 1, wherein the LCDR1 comprises the amino acid sequence of SEQ ID NO: 2.

3. The isolated antigen binding protein according to claim 1, wherein the antigen binding protein is an antibody or an antigen binding fragment thereof.

4. The isolated antigen binding protein according to claim 1, wherein the VL comprises framework regions L-FR1, L-FR2, L-FR3, and L-FR4, and the VH comprises H-FR1, H-FR2, H-FR3 and H-FR4, wherein the L-FR1 comprises the amino acid sequence of any one of SEQ ID NOs: 21-23, the L-FR2 comprises the amino acid sequence of any one of SEQ ID NOs: 24-25, the L-FR3 comprises the amino acid sequence of any one of SEQ ID NOs: 26-28, the L-FR4 comprises the amino acid sequence of any one of SEQ ID NOs: 29-30, the H-FR1 comprises the amino acid sequence of any one of SEQ ID NOs: 31-33, the H-FR2 comprises the amino acid sequence of any one of SEQ ID NOs: 34-35, the H-FR3 comprises the amino acid sequence of any one of SEQ ID NOs: 36-38, and the H-FR4 comprises the amino acid sequence of any one of SEQ ID NOs: 39-40.

5. The isolated antigen binding protein according to claim 1, comprising the VL and the VH, wherein
(a) the VL comprises the amino acid sequence of SEQ ID NO:41 and the VH comprises the amino acid sequence of SEQ ID NO:44;
(b) the VL comprises the amino acid sequence of SEQ ID NO:42 and the VH comprises the amino acid sequence of SEQ ID NO:45; or (c) the VL comprises the amino acid sequence of SEQ ID NO:43 and the VH comprises the amino acid sequence of SEQ ID NO:46.

6. The isolated antigen binding protein according to claim 1, comprising an antibody light chain constant region, and wherein the antibody light chain constant region comprises a human Kappa light chain constant region.

7. The isolated antigen binding protein according to claim 6, wherein the antibody light chain constant region comprises the amino acid sequence of SEQ ID NO: 47.

8. The isolated antigen binding protein according to claim 1, comprising an antibody heavy chain constant region, and the antibody heavy chain constant region is derived from a human IgG heavy chain constant region.

9. The isolated antigen binding protein according to claim 1, comprising an antibody light chain (LC) and an antibody heavy chain (HC), and wherein comprise
(a) the LC comprises the amino acid sequence of SEQ ID NOs:49 and the HC comprises the amino acid sequence of SEQ ID NO:50;
(b) the LC comprises the amino acid sequence of SEQ ID NO:51 and the HC comprises the amino acid sequence of SEQ ID NO:52; or
(c) the LC comprises the amino acid sequence of SEQ ID NO: 53 and the HC comprises the amino acid sequence of SEQ ID NO:54.

10. An immunoconjugate comprising the isolated antigen binding protein of claim 1.

11. A pharmaceutical composition comprising the isolated antigen binding protein of claim 1.

12. An isolated nucleic acid molecule encoding the isolated antigen binding protein according to claim 1.

13. A vector comprising the nucleic acid molecule according to claim 12.

14. An isolated cell comprising the nucleic acid molecule according to claim 12.

15. A method for detecting C5 in a sample, comprising: contacting the sample isolated from a subject with the isolated antigen binding protein of claim 1, wherein the antigen binding protein of claim 1 is labeled with a detectable label or a reporter molecule; and
detecting presence of an immunocomplex of the C5 protein and the antigen binding protein with the detectable label or reporter molecule in the sample by an immunoassay;

wherein the detectable label or reporter molecule is selected from the group consisting of a radioisotope, a fluorescent or chemiluminescent moiety, an enzyme and a biotin/avidin.

* * * * *

SEQUENCE LISTING

```
<160> NUMBER OF SEQ ID NOS: 71

<210> SEQ ID NO 1
<211> LENGTH: 15
<212> TYPE: PRT
<213> ORGANISM: Artificial Sequence
<220> FEATURE:
<223> OTHER INFORMATION: LCDR1

<400> SEQUENCE: 1

Lys Ala Ser Gln Ser Val Asp Tyr Asp Gly Asp Ser Tyr Leu Asn
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: LCDR1D32E

<400> SEQUENCE: 2

Lys Ala Ser Gln Ser Val Asp Tyr Glu Gly Asp Ser Tyr Leu Asn
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: LCDR1D32I

<400> SEQUENCE: 3

Lys Ala Ser Gln Ser Val Asp Tyr Ile Gly Asp Ser Tyr Leu Asn
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: LCDR1D32L

<400> SEQUENCE: 4

Lys Ala Ser Gln Ser Val Asp Tyr Leu Gly Asp Ser Tyr Leu Asn
1               5                   10                  15

<210> SEQ ID NO 5
```

```
<211> LENGTH: 15
<212> TYPE: PRT
<213> ORGANISM: Artificial Sequence
<220> FEATURE:
<223> OTHER INFORMATION: LCDR1D32G

<400> SEQUENCE: 5

Lys Ala Ser Gln Ser Val Asp Tyr Gly Gly Asp Ser Tyr Leu Asn
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: LCDR1D32S

<400> SEQUENCE: 6

Lys Ala Ser Gln Ser Val Asp Tyr Ser Gly Asp Ser Tyr Leu Asn
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: LCDR1D32T

<400> SEQUENCE: 7

Lys Ala Ser Gln Ser Val Asp Tyr Thr Gly Asp Ser Tyr Leu Asn
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: LCDR1D32V

<400> SEQUENCE: 8

Lys Ala Ser Gln Ser Val Asp Tyr Val Gly Asp Ser Tyr Leu Asn
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: LCDR1D32Y

<400> SEQUENCE: 9

Lys Ala Ser Gln Ser Val Asp Tyr Tyr Gly Asp Ser Tyr Leu Asn
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: LCDR1G33A

<400> SEQUENCE: 10

Lys Ala Ser Gln Ser Val Asp Tyr Asp Ala Asp Ser Tyr Leu Asn
1               5                   10                  15

<210> SEQ ID NO 11
<211> LENGTH: 15
```

```
<212> TYPE: PRT
<213> ORGANISM: Artificial Sequence
<220> FEATURE:
<223> OTHER INFORMATION: LCDR1G33S

<400> SEQUENCE: 11

Lys Ala Ser Gln Ser Val Asp Tyr Asp Ser Asp Ser Tyr Leu Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: LCDR1G33I

<400> SEQUENCE: 12

Lys Ala Ser Gln Ser Val Asp Tyr Asp Ile Asp Ser Tyr Leu Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: LCDR1G33Q

<400> SEQUENCE: 13

Lys Ala Ser Gln Ser Val Asp Tyr Asp Gln Asp Ser Tyr Leu Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: LCDR1G33T

<400> SEQUENCE: 14

Lys Ala Ser Gln Ser Val Asp Tyr Asp Thr Asp Ser Tyr Leu Asn
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: LCDR1G33V

<400> SEQUENCE: 15

Lys Ala Ser Gln Ser Val Asp Tyr Asp Val Asp Ser Tyr Leu Asn
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: LCDR2

<400> SEQUENCE: 16

Ala Ala Ser Asn Leu Glu Ser
1               5

<210> SEQ ID NO 17
<211> LENGTH: 9
<212> TYPE: PRT
```

-continued

<210> ORGANISM: Artificial Sequence
<220> FEATURE:
<223> OTHER INFORMATION: LCDR3

<400> SEQUENCE: 17

Gln Gln Ser Asn Glu Asp Pro Ser Thr
1               5

<210> SEQ ID NO 18
<211> LENGTH: 5
<212> TYPE: PRT
<213> ORGANISM: Artificial Sequence
<220> FEATURE:
<223> OTHER INFORMATION: HCDR1

<400> SEQUENCE: 18

Asn Tyr Gly Met Asn
1               5

<210> SEQ ID NO 19
<211> LENGTH: 17
<212> TYPE: PRT
<213> ORGANISM: Artificial Sequence
<220> FEATURE:
<223> OTHER INFORMATION: HCDR2

<400> SEQUENCE: 19

Trp Ile Asn Thr Tyr Thr Gly Glu Pro Thr Tyr Ala Asp Asp Phe Lys
1               5                   10                  15

Gly

<210> SEQ ID NO 20
<211> LENGTH: 13
<212> TYPE: PRT
<213> ORGANISM: Artificial Sequence
<220> FEATURE:
<223> OTHER INFORMATION: HCDR3

<400> SEQUENCE: 20

Thr Lys Val Pro Leu Tyr Phe Ala Tyr Ala Met Asp Tyr
1               5                   10

<210> SEQ ID NO 21
<211> LENGTH: 23
<212> TYPE: PRT
<213> ORGANISM: Artificial Sequence
<220> FEATURE:
<223> OTHER INFORMATION: L-FR1

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 22
<211> LENGTH: 23
<212> TYPE: PRT
<213> ORGANISM: Artificial Sequence
<220> FEATURE:
<223> OTHER INFORMATION: L-FR1

<400> SEQUENCE: 22

Asp Ile Val Leu Thr Gln Ser Pro Ser Ser Leu Ala Val Ser Leu Gly
1               5                   10                  15

```
Glu Arg Ala Thr Ile Asn Cys
            20

<210> SEQ ID NO 23
<211> LENGTH: 23
<212> TYPE: PRT
<213> ORGANISM: Artificial Sequence
<220> FEATURE:
<223> OTHER INFORMATION: L-FR1

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 24
<211> LENGTH: 15
<212> TYPE: PRT
<213> ORGANISM: Artificial Sequence
<220> FEATURE:
<223> OTHER INFORMATION: L-FR2

<400> SEQUENCE: 24

Trp Tyr Gln Gln Lys Pro Gly Gln Pro Pro Lys Leu Leu Ile Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: L-FR2

<400> SEQUENCE: 25

Trp Tyr Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Artificial Sequence
<220> FEATURE:
<223> OTHER INFORMATION: L-FR3

<400> SEQUENCE: 26

Gly Ile Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: L-FR3

<400> SEQUENCE: 27

Gly Ile Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 28
```

```
<211> LENGTH: 32
<212> TYPE: PRT
<213> ORGANISM: Artificial Sequence
<220> FEATURE:
<223> OTHER INFORMATION: L-FR3

<400> SEQUENCE: 28

Gly Ile Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 29
<211> LENGTH: 10
<212> TYPE: PRT
<213> ORGANISM: Artificial Sequence
<220> FEATURE:
<223> OTHER INFORMATION: L-FR4

<400> SEQUENCE: 29

Phe Gly Gly Gly Thr Lys Leu Glu Ile Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: L-FR4

<400> SEQUENCE: 30

Phe Gly Gly Gly Thr Lys Val Glu Ile Lys
1               5                   10

<210> SEQ ID NO 31
<211> LENGTH: 30
<212> TYPE: PRT
<213> ORGANISM: Artificial Sequence
<220> FEATURE:
<223> OTHER INFORMATION: H-FR1

<400> SEQUENCE: 31

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
                20                  25                  30

<210> SEQ ID NO 32
<211> LENGTH: 30
<212> TYPE: PRT
<213> ORGANISM: Artificial Sequence
<220> FEATURE:
<223> OTHER INFORMATION: H-FR1

<400> SEQUENCE: 32

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
                20                  25                  30

<210> SEQ ID NO 33
<211> LENGTH: 30
<212> TYPE: PRT
<213> ORGANISM: Artificial Sequence
<220> FEATURE:
<223> OTHER INFORMATION: H-FR1
```

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 34
<211> LENGTH: 14
<212> TYPE: PRT
<213> ORGANISM: Artificial Sequence
<220> FEATURE:
<223> OTHER INFORMATION: H-FR2

<400> SEQUENCE: 34

Trp Val Lys Gln Ala Pro Gly Lys Gly Leu Lys Trp Met Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: H-FR2

<400> SEQUENCE: 35

Trp Val Arg Gln Ala Pro Gly Gln Gly Leu Glu Trp Met Gly
1               5                   10

<210> SEQ ID NO 36
<211> LENGTH: 32
<212> TYPE: PRT
<213> ORGANISM: Artificial Sequence
<220> FEATURE:
<223> OTHER INFORMATION: H-FR3

<400> SEQUENCE: 36

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Thr Arg
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: H-FR3

<400> SEQUENCE: 37

Arg Phe Val Phe Ser Leu Asp Thr Ser Val Ser Met Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: H-FR3

<400> SEQUENCE: 38

Arg Phe Thr Phe Thr Leu Asp Thr Ser Thr Ser Thr Ala Tyr Leu Glu
1               5                   10                  15

-continued

```
Leu Ser Ser Leu Arg Ser Glu Asp Thr Ala Val Tyr Tyr Cys Ala Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: H-FR4

<400> SEQUENCE: 39

Trp Gly Gln Gly Thr Ser Val Thr Val Ser Ser
1               5                   10

<210> SEQ ID NO 40
<211> LENGTH: 11
<212> TYPE: PRT
<213> ORGANISM: Artificial Sequence
<220> FEATURE:
<223> OTHER INFORMATION: H-FR4

<400> SEQUENCE: 40

Trp Gly Gln Gly Thr Leu Val Thr Val Ser Ser
1               5                   10

<210> SEQ ID NO 41
<211> LENGTH: 111
<212> TYPE: PRT
<213> ORGANISM: Artificial Sequence
<220> FEATURE:
<223> OTHER INFORMATION: VL

<400> SEQUENCE: 41

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Ser Thr Phe Gly Gly Gly Thr Lys Leu Glu Ile Lys
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: VL

<400> SEQUENCE: 42

Asp Ile Val Leu Thr Gln Ser Pro Ser Ser Leu Ala Val Ser Leu Gly
1               5                   10                  15

Glu Arg Ala Thr Ile Asn Cys Lys Ala Ser Gln Ser Val Asp Tyr Glu
            20                  25                  30

Gly Asp Ser Tyr Leu Asn Trp Tyr Gln Gln Lys Pro Gly Gln Pro Pro
        35                  40                  45
```

-continued

```
Lys Leu Leu Ile Tyr Ala Ala Ser Asn Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Ser Thr Phe Gly Gly Gly Thr Lys Val Glu Ile Lys
                100                 105                 110
```

<210> SEQ ID NO 43
<211> LENGTH: 111
<212> TYPE: PRT
<213> ORGANISM: Artificial Sequence
<220> FEATURE:
<223> OTHER INFORMATION: VL

<400> SEQUENCE: 43

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
                20                  25                  30

Gly Asp Ser Tyr Leu Asn Trp Tyr Gln Gln Lys Pro Gly Lys Pro Pro
            35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Ser Thr Phe Gly Gly Gly Thr Lys Val Glu Ile Lys
                100                 105                 110
```

<210> SEQ ID NO 44
<211> LENGTH: 122
<212> TYPE: PRT
<213> ORGANISM: Artificial Sequence
<220> FEATURE:
<223> OTHER INFORMATION: VH

<400> SEQUENCE: 44

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Thr Lys Val Pro Leu Tyr Phe Ala Tyr Ala Met Asp Tyr Trp
                100                 105                 110

Gly Gln Gly Thr Ser Val Thr Val Ser Ser
            115                 120
```

```
<210> SEQ ID NO 45
<211> LENGTH: 122
<212> TYPE: PRT
<213> ORGANISM: Artificial Sequence
<220> FEATURE:
<223> OTHER INFORMATION: VH

<400> SEQUENCE: 45

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Met Ala Tyr
65                  70                  75                  80

Leu Gln Ile Ser Ser Leu Lys Ala Glu Asp Thr Ala Val Tyr Tyr Cys
                85                  90                  95

Ala Arg Thr Lys Val Pro Leu Tyr Phe Ala Tyr Ala Met Asp Tyr Trp
                100                 105                 110

Gly Gln Gly Thr Leu Val Thr Val Ser Ser
            115                 120

<210> SEQ ID NO 46
<211> LENGTH: 122
<212> TYPE: PRT
<213> ORGANISM: Artificial Sequence
<220> FEATURE:
<223> OTHER INFORMATION: VH

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Thr Phe Thr Leu Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Thr Lys Val Pro Leu Tyr Phe Ala Tyr Ala Met Asp Tyr Trp
                100                 105                 110

Gly Gln Gly Thr Leu Val Thr Val Ser Ser
            115                 120

<210> SEQ ID NO 47
<211> LENGTH: 107
<212> TYPE: PRT
<213> ORGANISM: Artificial Sequence
<220> FEATURE:
<223> OTHER INFORMATION: CL

<400> SEQUENCE: 47

Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 48
<211> LENGTH: 330
<212> TYPE: PRT
<213> ORGANISM: Artificial Sequence
<220> FEATURE:
<223> OTHER INFORMATION: CH

<400> SEQUENCE: 48

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 218
<212> TYPE: PRT
<213> ORGANISM: Artificial Sequence
<220> FEATURE:
<223> OTHER INFORMATION: Lc

<400> SEQUENCE: 49

Asp Ile Val Leu Thr Gln Ser Pro Ala Ser Leu Ala Val Ser Leu Gly
1                   5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Ser Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
        210                 215

<210> SEQ ID NO 50
<211> LENGTH: 452
<212> TYPE: PRT
<213> ORGANISM: Artificial Sequence
<220> FEATURE:
<223> OTHER INFORMATION: Hc

<400> SEQUENCE: 50

Gln Ile Gln Leu Val Gln Ser Gly Pro Glu Leu Lys Lys Pro Gly Glu
1                   5                   10                  15

Thr Val Lys Ile Ser Cys Lys Ala Ser Gly Tyr Thr Phe Thr Asn Tyr

-continued

```
                    20                  25                  30
Gly Met Asn Trp Val Lys Gln Ala Pro Gly Lys Gly Leu Lys Trp Met
                35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Thr Lys Val Pro Leu Tyr Phe Ala Tyr Ala Met Asp Tyr Trp
            100                 105                 110

Gly Gln Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445
```

-continued

```
Ser Pro Gly Lys
    450

<210> SEQ ID NO 51
<211> LENGTH: 218
<212> TYPE: PRT
<213> ORGANISM: Artificial Sequence
<220> FEATURE:
<223> OTHER INFORMATION: Lc

<400> SEQUENCE: 51

Asp Ile Val Leu Thr Gln Ser Pro Ser Ser Leu Ala Val Ser Leu Gly
1               5                   10                  15

Glu Arg Ala Thr Ile Asn Cys Lys Ala Ser Gln Ser Val Asp Tyr Glu
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 52
<211> LENGTH: 452
<212> TYPE: PRT
<213> ORGANISM: Artificial Sequence
<220> FEATURE:
<223> OTHER INFORMATION: Hc

<400> SEQUENCE: 52

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Met Ala Tyr
```

-continued

```
65                  70                  75                  80

Leu Gln Ile Ser Ser Leu Lys Ala Glu Asp Thr Ala Val Tyr Tyr Cys
                85                  90                  95

Ala Arg Thr Lys Val Pro Leu Tyr Phe Ala Tyr Ala Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
        450
```

<210> SEQ ID NO 53
<211> LENGTH: 218
<212> TYPE: PRT
<213> ORGANISM: Artificial Sequence -continued

```
<220> FEATURE:
<223> OTHER INFORMATION: Lc

<400> SEQUENCE: 53

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
                20                  25                  30

Gly Asp Ser Tyr Leu Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 54
<211> LENGTH: 452
<212> TYPE: PRT
<213> ORGANISM: Artificial Sequence
<220> FEATURE:
<223> OTHER INFORMATION: Hc

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
    50                  55                  60

Lys Gly Arg Phe Thr Phe Thr Leu Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Thr Lys Val Pro Leu Tyr Phe Ala Tyr Ala Met Asp Tyr Trp
            100                 105                 110

Gly Gln Gly Thr Leu Val Thr Val Ser Ser Ala Ser Thr Lys Gly Pro
```

-continued

```
            115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Ala Ala
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450
```

<210> SEQ ID NO 55
<211> LENGTH: 214
<212> TYPE: PRT
<213> ORGANISM: Artificial Sequence
<220> FEATURE:
<223> OTHER INFORMATION: Lc

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
```

66

-continued

```
                  20                  25                  30

Leu Asn Trp Tyr Gln Gln Lys Pro Gly Lys Ala Pro Lys Leu Leu Ile
              35                  40                  45

Tyr Gly Ala Thr Asn Leu Ala Asp Gly Val Pro Ser Arg Phe Ser Gly
          50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                  85                  90                  95

Thr Phe Gly Gln Gly Thr Lys Val Glu Ile Lys Arg Thr Val Ala Ala
              100                 105                 110

Pro Ser Val Phe Ile Phe Pro Pro Ser Asp Glu Gln Leu Lys Ser Gly
          115                 120                 125

Thr Ala Ser Val Val Cys Leu Leu Asn Asn Phe Tyr Pro Arg Glu Ala
      130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                  165                 170                 175

Ser Thr Leu Thr Leu Ser Lys Ala Asp Tyr Glu Lys His Lys Val Tyr
              180                 185                 190

Ala Cys Glu Val Thr His Gln Gly Leu Ser Ser Pro Val Thr Lys Ser
          195                 200                 205

Phe Asn Arg Gly Glu Cys
      210
```

<210> SEQ ID NO 56
<211> LENGTH: 448
<212> TYPE: PRT
<213> ORGANISM: Artificial Sequence
<220> FEATURE:
<223> OTHER INFORMATION: Hc

<400> SEQUENCE: 56

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ile Phe Ser Asn Tyr
              20                  25                  30

Trp Ile Gln Trp Val Arg Gln Ala Pro Gly Gln Gly Leu Glu Trp Met
          35                  40                  45

Gly Glu Ile Leu Pro Gly Ser Gly Ser Thr Glu Tyr Thr Glu Asn Phe
      50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                  85                  90                  95

Ala Arg Tyr Phe Phe Gly Ser Ser Pro Asn Trp Tyr Phe Asp Val Trp
              100                 105                 110

Gly Gln Gly Thr Leu Val Thr Val Ser Ser Ala Ser Thr Lys Gly Pro
          115                 120                 125

Ser Val Phe Pro Leu Ala Pro Cys Ser Arg Ser Thr Ser Glu Ser Thr
      130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

-continued

```
                    165                 170                 175
Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
                195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445
```

<210> SEQ ID NO 57
<211> LENGTH: 448
<212> TYPE: PRT
<213> ORGANISM: Artificial Sequence
<220> FEATURE:
<223> OTHER INFORMATION: Hc

<400> SEQUENCE: 57

```
Gln Val Gln Leu Val Gln Ser Gly Ala Glu Val Lys Lys Pro Gly Ala
1                   5                   10                  15

Ser Val Lys Val Ser Cys Lys Ala Ser Gly His Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

-continued

```
                85                    90                    95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
            210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
            435                 440                 445
```

<210> SEQ ID NO 58
<211> LENGTH: 217
<212> TYPE: PRT
<213> ORGANISM: Artificial Sequence
<220> FEATURE:
<223> OTHER INFORMATION: Lc

<400> SEQUENCE: 58

Asp Ile Gln Met Thr Gln Ser Pro Ser Ser Leu Ser Ala Ser Val Gly

-continued

```
1               5               10              15
Asp Arg Val Thr Ile Thr Cys Arg Ala Ser Gln Gly Ile Ser Ser Ser
            20              25              30

Leu Ala Trp Tyr Gln Gln Lys Pro Gly Lys Ala Pro Lys Leu Leu Ile
            35              40              45

Tyr Gly Ala Ser Glu Thr Glu Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Asn Thr Lys Val Gly Ser Ser
            85              90              95

Tyr Gly Asn Thr Phe Gly Gly Gly Thr Lys Val Glu Ile Lys Arg Thr
            100             105             110

Val Ala Ala Pro Ser Val Phe Ile Phe Pro Pro Ser Asp Glu Gln Leu
            115             120             125

Lys Ser Gly Thr Ala Ser Val Val Cys Leu Leu Asn Asn Phe Tyr Pro
    130             135             140

Arg Glu Ala Lys Val Gln Trp Lys Val Asp Asn Ala Leu Gln Ser Gly
145             150             155             160

Asn Ser Gln Glu Ser Val Thr Glu Gln Asp Ser Lys Asp Ser Thr Tyr
            165             170             175

Ser Leu Ser Ser Thr Leu Thr Leu Ser Lys Ala Asp Tyr Glu Lys His
            180             185             190

Lys Val Tyr Ala Cys Glu Val Thr His Gln Gly Leu Ser Ser Pro Val
            195             200             205

Thr Lys Ser Phe Asn Arg Gly Glu Cys
    210             215
```

```
<210> SEQ ID NO 59
<211> LENGTH: 451
<212> TYPE: PRT
<213> ORGANISM: Artificial Sequence
<220> FEATURE:
<223> OTHER INFORMATION: Hc

<400> SEQUENCE: 59
```

```
Gln Val Gln Leu Val Glu Ser Gly Gly Gly Leu Val Gln Pro Gly Arg
1               5               10              15

Ser Leu Arg Leu Ser Cys Ala Ala Ser Gly Phe Thr Val His Ser Ser
            20              25              30

Tyr Tyr Met Ala Trp Val Arg Gln Ala Pro Gly Lys Gly Leu Glu Trp
            35              40              45

Val Gly Ala Ile Phe Thr Gly Ser Gly Ala Glu Tyr Lys Ala Glu Trp
    50              55              60

Ala Lys Gly Arg Val Thr Ile Ser Lys Asp Thr Ser Lys Asn Gln Val
65              70              75              80

Val Leu Thr Met Thr Asn Met Asp Pro Val Asp Thr Ala Thr Tyr Tyr
            85              90              95

Cys Ala Ser Asp Ala Gly Tyr Asp Tyr Pro Thr His Ala Met His Tyr
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
```

-continued

```
    145                 150                 155                 160
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Leu His Glu Ala Leu His Ala His Tyr Thr Arg Lys Glu Leu Ser
        435                 440                 445

Leu Ser Pro
    450

<210> SEQ ID NO 60
<211> LENGTH: 1676
<212> TYPE: PRT
<213> ORGANISM: Artificial Sequence
<220> FEATURE:
<223> OTHER INFORMATION: Ag

<400> SEQUENCE: 60

Met Gly Leu Leu Gly Ile Leu Cys Phe Leu Ile Phe Leu Gly Lys Thr
1                   5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
```

-continued

```
              50                    55                    60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
               100                 105                 110

Lys Ser Lys Arg Met Pro Ile Thr Tyr Asp Asn Gly Phe Leu Phe Ile
           115                 120                 125

His Thr Asp Lys Pro Val Tyr Thr Pro Asp Gln Ser Val Lys Val Arg
       130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
               165                 170                 175

Ile Asp His Ile Gly Ile Ile Ser Phe Pro Asp Phe Lys Ile Pro Ser
           180                 185                 190

Asn Pro Arg Tyr Gly Met Trp Thr Ile Lys Ala Lys Tyr Lys Glu Asp
           195                 200                 205

Phe Ser Thr Thr Gly Thr Ala Tyr Phe Glu Val Lys Glu Tyr Val Leu
       210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
               245                 250                 255

Asn Lys Val Val Thr Glu Ala Asp Val Tyr Ile Thr Phe Gly Ile Arg
           260                 265                 270

Glu Asp Leu Lys Asp Asp Gln Lys Glu Met Met Gln Thr Ala Met Gln
           275                 280                 285

Asn Thr Met Leu Ile Asn Gly Ile Ala Gln Val Thr Phe Asp Ser Glu
       290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
               325                 330                 335

Ser Glu Glu Ala Glu Ile Pro Gly Ile Lys Tyr Val Leu Ser Pro Tyr
           340                 345                 350

Lys Leu Asn Leu Val Ala Thr Pro Leu Phe Leu Lys Pro Gly Ile Pro
           355                 360                 365

Tyr Pro Ile Lys Val Gln Val Lys Asp Ser Leu Asp Gln Leu Val Gly
       370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
           405                 410                 415

Val Ala Ser Phe Val Leu Asn Leu Pro Ser Gly Val Thr Val Leu Glu
           420                 425                 430

Phe Asn Val Lys Thr Asp Ala Pro Asp Leu Pro Glu Glu Asn Gln Ala
       435                 440                 445

Arg Glu Gly Tyr Arg Ala Ile Ala Tyr Ser Ser Leu Ser Gln Ser Tyr
       450                 455                 460

Leu Tyr Ile Asp Trp Thr Asp Asn His Lys Ala Leu Leu Val Gly Glu
465                 470                 475                 480
```

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
        530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
            595                 600                 605

Val Tyr Gly Val Gln Arg Gly Ala Lys Lys Pro Leu Glu Arg Val Phe
        610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
            675                 680                 685

Lys Tyr Lys His Ser Val Val Lys Lys Cys Cys Tyr Asp Gly Ala Cys
        690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
        770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
        850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Ser His Leu Val
                885                 890                 895

-continued

```
Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
                980                 985                 990

Ser Gln Glu Gly Ile Asn Ile Leu  Thr His Leu Pro Lys  Gly Ser Ala
        995                 1000                1005

Glu Ala  Glu Leu Met Ser Val  Val Pro Val Phe Tyr  Val Phe His
    1010                1015                1020

Tyr Leu  Glu Thr Gly Asn His  Trp Asn Ile Phe His  Ser Asp Pro
    1025                1030                1035

Leu Ile  Glu Lys Gln Lys Leu  Lys Lys Lys Leu Lys  Glu Gly Met
    1040                1045                1050

Leu Ser  Ile Met Ser Tyr Arg  Asn Ala Asp Tyr Ser  Tyr Ser Val
    1055                1060                1065

Trp Lys  Gly Gly Ser Ala Ser  Thr Trp Leu Thr Ala  Phe Ala Leu
    1070                1075                1080

Arg Val  Leu Gly Gln Val Asn  Lys Tyr Val Glu Gln  Asn Gln Asn
    1085                1090                1095

Ser Ile  Cys Asn Ser Leu Leu  Trp Leu Val Glu Asn  Tyr Gln Leu
    1100                1105                1110

Asp Asn  Gly Ser Phe Lys Glu  Asn Ser Gln Tyr Gln  Pro Ile Lys
    1115                1120                1125

Leu Gln  Gly Thr Leu Pro Val  Glu Ala Arg Glu Asn  Ser Leu Tyr
    1130                1135                1140

Leu Thr  Ala Phe Thr Val Ile  Gly Ile Arg Lys Ala  Phe Asp Ile
    1145                1150                1155

Cys Pro  Leu Val Lys Ile Asp  Thr Ala Leu Ile Lys  Ala Asp Asn
    1160                1165                1170

Phe Leu  Leu Glu Asn Thr Leu  Pro Ala Gln Ser Thr  Phe Thr Leu
    1175                1180                1185

Ala Ile  Ser Ala Tyr Ala Leu  Ser Leu Gly Asp Lys  Thr His Pro
    1190                1195                1200

Gln Phe  Arg Ser Ile Val Ser  Ala Leu Lys Arg Glu  Ala Leu Val
    1205                1210                1215

Lys Gly  Asn Pro Pro Ile Tyr  Arg Phe Trp Lys Asp  Asn Leu Gln
    1220                1225                1230

His Lys  Asp Ser Ser Val Pro  Asn Thr Gly Thr Ala  Arg Met Val
    1235                1240                1245

Glu Thr  Thr Ala Tyr Ala Leu  Leu Thr Ser Leu Asn  Leu Lys Asp
    1250                1255                1260

Ile Asn  Tyr Val Asn Pro Val  Ile Lys Trp Leu Ser  Glu Glu Gln
    1265                1270                1275

Arg Tyr  Gly Gly Gly Phe Tyr  Ser Thr Gln Asp Thr  Ile Asn Ala
    1280                1285                1290

Ile Glu  Gly Leu Thr Glu Tyr  Ser Leu Leu Val Lys  Gln Leu Arg
```

-continued

```
        1295              1300              1305

Leu Ser Met Asp Ile Asp Val Ser Tyr Lys His Lys Gly Ala Leu
    1310             1315             1320

His Asn Tyr Lys Met Thr Asp Lys Asn Phe Leu Gly Arg Pro Val
    1325             1330             1335

Glu Val Leu Leu Asn Asp Asp Leu Ile Val Ser Thr Gly Phe Gly
    1340             1345             1350

Ser Gly Leu Ala Thr Val His Val Thr Thr Val Val His Lys Thr
    1355             1360             1365

Ser Thr Ser Glu Glu Val Cys Ser Phe Tyr Leu Lys Ile Asp Thr
    1370             1375             1380

Gln Asp Ile Glu Ala Ser His Tyr Arg Gly Tyr Gly Asn Ser Asp
    1385             1390             1395

Tyr Lys Arg Ile Val Ala Cys Ala Ser Tyr Lys Pro Ser Arg Glu
    1400             1405             1410

Glu Ser Ser Ser Gly Ser Ser His Ala Val Met Asp Ile Ser Leu
    1415             1420             1425

Pro Thr Gly Ile Ser Ala Asn Glu Glu Asp Leu Lys Ala Leu Val
    1430             1435             1440

Glu Gly Val Asp Gln Leu Phe Thr Asp Tyr Gln Ile Lys Asp Gly
    1445             1450             1455

His Val Ile Leu Gln Leu Asn Ser Ile Pro Ser Ser Asp Phe Leu
    1460             1465             1470

Cys Val Arg Phe Arg Ile Phe Glu Leu Phe Glu Val Gly Phe Leu
    1475             1480             1485

Ser Pro Ala Thr Phe Thr Val Tyr Glu Tyr His Arg Pro Asp Lys
    1490             1495             1500

Gln Cys Thr Met Phe Tyr Ser Thr Ser Asn Ile Lys Ile Gln Lys
    1505             1510             1515

Val Cys Glu Gly Ala Ala Cys Lys Cys Val Glu Ala Asp Cys Gly
    1520             1525             1530

Gln Met Gln Glu Glu Leu Asp Leu Thr Ile Ser Ala Glu Thr Arg
    1535             1540             1545

Lys Gln Thr Ala Cys Lys Pro Glu Ile Ala Tyr Ala Tyr Lys Val
    1550             1555             1560

Ser Ile Thr Ser Ile Thr Val Glu Asn Val Phe Val Lys Tyr Lys
    1565             1570             1575

Ala Thr Leu Leu Asp Ile Tyr Lys Thr Gly Glu Ala Val Ala Glu
    1580             1585             1590

Lys Asp Ser Glu Ile Thr Phe Ile Lys Lys Val Thr Cys Thr Asn
    1595             1600             1605

Ala Glu Leu Val Lys Gly Arg Gln Tyr Leu Ile Met Gly Lys Glu
    1610             1615             1620

Ala Leu Gln Ile Lys Tyr Asn Phe Ser Phe Arg Tyr Ile Tyr Pro
    1625             1630             1635

Leu Asp Ser Leu Thr Trp Ile Glu Tyr Trp Pro Arg Asp Thr Thr
    1640             1645             1650

Cys Ser Ser Cys Gln Ala Phe Leu Ala Asn Leu Asp Glu Phe Ala
    1655             1660             1665

Glu Asp Ile Phe Leu Asn Gly Cys
    1670             1675
```

<210> SEQ ID NO 61

-continued

```
<211> LENGTH: 366
<212> TYPE: DNA
<213> ORGANISM: Artificial Sequence
<220> FEATURE:
<223> OTHER INFORMATION: VH

<400> SEQUENCE: 61
caggtgcagc tggtgcagtc cggcagcgag ctgaagaagc caggcgcctc tgtgaaggtg      60
tcctgtaagg ctagcggcta caccttcaca aactatggca tgaattgggt gaggcaggct     120
cctggacagg gcctggagtg gatgggctgg atcaacacct acacaggcga gccaacatat     180
gccgacgact tcaagggccg gttcgtgttt agcctggaca cctccgtgtc catggcttac     240
ctgcagatct ccagcctgaa ggccgaggat acagccgtgt actattgcgc caggaccaag     300
gtgcctctgt acttcgccta tgctatggac tattggggcc agggcacact ggtgaccgtg     360
tcttcc                                                              366

<210> SEQ ID NO 62
<211> LENGTH: 366
<212> TYPE: DNA
<213> ORGANISM: Artificial Sequence
<220> FEATURE:
<223> OTHER INFORMATION: VH

<400> SEQUENCE: 62
caggttcagc tggttcagtc tggcgccgaa gtgaagaaac ctggcgcctc tgtgaaggtg      60
tcctgcaagg cttctggcta cacctttacc aactacggca tgaactgggt ccgacaggct     120
cctggacaag gcctggaatg gatgggctgg atcaacacct ataccggcga gcctacctac     180
gccgacgact tcaagggcag attcacattc accctggaca cctccaccag caccgcctat     240
ctggaactgt ccagcctgag atctgaggac accgccgtgt actactgcgc cagaacaaag     300
gtgcccctgt acttcgccta cgccatggat tattggggcc agggcacact ggtcaccgtg     360
tcatct                                                              366

<210> SEQ ID NO 63
<211> LENGTH: 333
<212> TYPE: DNA
<213> ORGANISM: Artificial Sequence
<220> FEATURE:
<223> OTHER INFORMATION: VL

<400> SEQUENCE: 63
gatatcgtgc tgacccagtc tccatcttcc ctggccgtgt ctctgggaga gagggctaca      60
atcaactgta aggcctccca gagcgtggac tacgagggcg actcctacct gaattggtat     120
cagcagaagc ccggccagcc ccctaagctg ctgatctatg ccgctagcaa cctggagtct     180
ggcatccctg ataggttctc tggctccggc agcggcaccg actttaccct gacaatctcc     240
agcctgcagg ctgaggatgt ggccgtgtac tattgccagc agtctaatga ggacccttcc     300
accttcggcg gcggcacaaa ggtggagatc aag                                333

<210> SEQ ID NO 64
<211> LENGTH: 333
<212> TYPE: DNA
<213> ORGANISM: Artificial Sequence
<220> FEATURE:
<223> OTHER INFORMATION: VL

<400> SEQUENCE: 64
gacatccagc tgacccagtc tccatcctct ctgtccgcct ctgtgggcga cagagtgacc      60
```

-continued

```
atcacatgca aggcctctca gtccgtggac tacgagggcg actcttacct gaactggtat        120
cagcagaagc ccggcaaggc ccctaagctg ctgatctacg ccgcctccaa tctggaatct       180
ggcatcccct ctagattctc cggctctggc tctggcaccg actttaccct gacaatctcc       240
agcctgcagc ctgaggactt cgccacctac tactgccagc agtccaacga ggacccctct       300
acatttggcg gaggcaccaa ggtggaaatc aag                                     333

<210> SEQ ID NO 65
<211> LENGTH: 654
<212> TYPE: DNA
<213> ORGANISM: Artificial Sequence
<220> FEATURE:
<223> OTHER INFORMATION: Lc

<400> SEQUENCE: 65
gatatcgtgc tgacccagtc tccatcttcc ctggccgtgt ctctgggaga gagggctaca         60
atcaactgta aggcctccca gagcgtggac tacgagggcg actcctacct gaattggtat        120
cagcagaagc ccggccagcc ccctaagctg ctgatctatg ccgctagcaa cctggagtct       180
ggcatccctg ataggttctc tggctccggc agcggcaccg actttaccct gacaatctcc       240
agcctgcagg ctgaggatgt ggccgtgtac tattgccagc agtctaatga ggacccttcc       300
accttcggcg gcggcacaaa ggtggagatc aagcgtacgg tggctgcacc atctgtcttc       360
atcttcccgc catctgatga gcagttgaaa tctggaactg cctctgttgt gtgcctgctg       420
aataacttct accccagaga agccaaagtc cagtggaagg tggacaacgc cctgcagagc       480
ggaaacagcc aggaaagcgt gacagagcag gattccaagg attccacata cagcctgagc       540
agcacactga cactgtccaa ggccgactac gagaagcaca aggtgtacgc ctgcgaagtg       600
acacaccagg gactgtcctc ccctgtgaca aagagcttca cagaggagaa atgc            654

<210> SEQ ID NO 66
<211> LENGTH: 1356
<212> TYPE: DNA
<213> ORGANISM: Artificial Sequence
<220> FEATURE:
<223> OTHER INFORMATION: Hc

<400> SEQUENCE: 66
caggtgcagc tggtgcagtc cggcagcgag ctgaagaagc caggcgcctc tgtgaaggtg         60
tcctgtaagg ctagcggcta caccttcaca aactatggca tgaattgggt gaggcaggct       120
cctggacagg gcctggagtg gatgggctgg atcaacacct acacaggcga gccaacatat       180
gccgacgact tcaagggccg gttcgtgttt agcctggaca cctccgtgtc catggcttac       240
ctgcagatct ccagcctgaa ggccgaggat acagccgtgt actattgcgc caggaccaag       300
gtgcctctgt acttcgccta tgctatggac tattggggcc agggcacact ggtgaccgtg       360
tcttccgcgt cgaccaaagg cccctccgtg tttcctctgg cccctcctc caagtctacc       420 tccggcggta ccgccgccct cggttgtttg gtcaaagact acttccccga gcccgtgacc       480
gtctcctgga actccggcgc cctgacctcc ggcgtgcaca cattccccgc cgtcctgcag       540
tcctccggcc tgtactctct gtcttccgtg gtgaccgtgc cctccagctc tttaggcaca       600
cagacctaca tctgcaacgt gaaccacaag ccctccaata ccaaggtgga caagagagtg       660
gagcccaagt cttgtgacaa gacacacact tgtcctcctt gtcccgctcc cgaagccgcc       720
ggaggcccta gcgtgttttt attcccccct aaacctaagg acaccctcat gatcagccgt       780
```

-continued

```
accccccgaag tgacttgtgt ggtggtggac gtgtcccacg aggaccccga agtcaagttc      840
aactggtacg tggacggcgt ggaggtgcat aatgccaaga ccaagccccg ggaggagcag      900
tataatagca cctatagggt ggtgtccgtg ctgaccgtgc tgcaccaaga ttggctgaac      960
ggcaaggagt acaagtgtaa ggtgtccaac aaggctttac ccgctcccat cgagaagacc     1020
atctccaagg ctaagggaca gcctcgtgag cctcaagttt atactttacc cccttctcgt     1080
gaggagatga ccaagaacca agtttcttta acatgtttag tgaagggctt ctacccctcc     1140
gacatcgccg tggagtggga gagcaatgga cagcccgaga caactacaa gaccacaccc      1200 cccgttttag acagcgacgg ctccttcttt ttatactcca agctcaccgt ggataagtcc     1260
cggtggcagc aaggtaacgt cttctcttgt tccgtgatgc acgaagcttt acacaaccat     1320
tacacccaga gtctttatc tttaagcccc ggcaag                               1356
```

<210> SEQ ID NO 67
<211> LENGTH: 654
<212> TYPE: DNA
<213> ORGANISM: Artificial Sequence
<220> FEATURE:
<223> OTHER INFORMATION: Lc

<400> SEQUENCE: 67

```
gacatccagc tgacccagtc tccatcctct ctgtccgcct ctgtgggcga cagagtgacc       60
atcacatgca aggcctctca gtccgtggac tacgagggcg actcttacct gaactggtat      120
cagcagaagc ccggcaaggc ccctaagctg ctgatctacg ccgcctccaa tctggaatct      180
ggcatcccct ctagattctc cggctctggc tctggcaccg actttaccct gacaatctcc      240
agcctgcagc ctgaggactt cgccacctac tactgccagc agtccaacga ggacccctct      300
acatttggcg gaggcaccaa ggtggaaatc aagcgtacgg tggctgcacc atctgtcttc      360
atcttcccgc catctgatga gcagttgaaa tctggaactg cctctgttgt gtgcctgctg      420
aataacttct accccagaga agccaaagtg cagtggaagg tggacaacgc cctgcagagc      480
ggaaacagcc aggaaagcgt gacagagcag gattccaagg attccacata cagcctgagc      540
agcacactga cactgtccaa ggccgactac gagaagcaca aggtgtacgc ctgcgaagtg      600
acacaccagg gactgtcctc ccctgtgaca aagagcttca cagaggaga atgc            654
```

<210> SEQ ID NO 68
<211> LENGTH: 1356
<212> TYPE: DNA
<213> ORGANISM: Artificial Sequence
<220> FEATURE:
<223> OTHER INFORMATION: Hc

<400> SEQUENCE: 68

```
caggttcagc tggttcagtc tggcgccgaa gtgaagaaac ctggcgcctc tgtgaaggtg       60
tcctgcaagg cttctggcta cacctttacc aactacggca tgaactgggt ccgacaggct      120
cctggacaag gcctggaatg gatgggctgg atcaacacct ataccggcga gcctacctac      180
gccgacgact tcaagggcag attcacattc accctggaca cctccaccag caccgcctat      240
ctggaactgt ccagcctgag atctgaggac accgccgtgt actactgcgc cagaacaaag      300
gtgcccctgt acttcgccta cgccatggat tattggggcc agggcacact ggtcaccgtg      360
tcatctgcgt cgaccaaagg cccctccgtg tttcctctgg cccctcctc caagtctacc      420 tccggcggta ccgccgccct cggttgtttg gtcaaagact acttccccga gcccgtgacc      480
gtctcctgga actccggcgc cctgacctcc ggcgtgcaca cattccccgc cgtcctgcag      540
```

-continued

```
tcctccggcc tgtactctct gtcttccgtg gtgaccgtgc cctccagctc tttaggcaca      600
cagacctaca tctgcaacgt gaaccacaag ccctccaata ccaaggtgga caagagagtg      660
gagcccaagt cttgtgacaa gacacacact tgtcctcctt gtcccgctcc cgaagccgcc      720
ggaggcccta gcgtgttttt attcccccct aaacctaagg acaccctcat gatcagccgt      780
acccccgaag tgacttgtgt ggtggtggac gtgtcccacg aggaccccga agtcaagttc      840
aactggtacg tggacggcgt ggaggtgcat aatgccaaga ccaagccccg ggaggagcag      900
tataatagca cctatagggt ggtgtccgtg ctgaccgtgc tgcaccaaga ttggctgaac      960
ggcaaggagt acaagtgtaa ggtgtccaac aaggctttac ccgctcccat cgagaagacc     1020
atctccaagg ctaagggaca gcctcgtgag cctcaagttt atactttacc cccttctcgt     1080
gaggagatga ccaagaacca gtttctttta acatgtttag tgaagggctt ctacccctcc     1140
gacatcgccg tggagtggga gagcaatgga cagcccgaga caactacaa gaccacaccc     1200 cccgttttag acagcgacgg ctccttcttt ttatactcca agctcaccgt ggataagtcc     1260
cggtggcagc aagtaacgt cttctcttgt tccgtgatgc acgaagcttt acacaaccat     1320
tacacccaga agtctttatc tttaagcccc ggcaag                              1356
```

```
<210> SEQ ID NO 69
<211> LENGTH: 15
<212> TYPE: PRT
<213> ORGANISM: Artificial Sequence
<220> FEATURE:
<223> OTHER INFORMATION: LCDR1; LCDR1D32E; LCDR1D32I; LCDR1D32L;
      LCDR1D32G; LCDR1D32S; LCDR1D32T; LCDR1D32V; LCDR1D32Y; LCDR1G33A;
      LCDR1G33S; LCDR1G33I; LCDR1G33Q; LCDR1G33T; LCDR1G33V
<220> FEATURE:
<221> NAME/KEY: misc_feature
<222> LOCATION: (9)..(9)
<223> OTHER INFORMATION: Xaa = Asp, Glu, Gly, Ile, Leu, Ser, Thr, Val,
      or Tyr
<220> FEATURE:
<221> NAME/KEY: misc_feature
<222> LOCATION: (10)..(10)
<223> OTHER INFORMATION: Xaa = Ala, Gly, Ile, Gln, Ser, Thr, or Val

<400> SEQUENCE: 69

Lys Ala Ser Gln Ser Val Asp Tyr Xaa Xaa Asp Ser Tyr Leu Asn
1               5                   10                  15

<210> SEQ ID NO 70
<211> LENGTH: 111
<212> TYPE: PRT
<213> ORGANISM: Artificial Sequence
<220> FEATURE:
<223> OTHER INFORMATION: CHI-16VL; 16H1L2mVL; 16H46L39amVL
<220> FEATURE:
<221> NAME/KEY: misc_feature
<222> LOCATION: (3)..(3)
<223> OTHER INFORMATION: Xaa = Gln, or Val
<220> FEATURE:
<221> NAME/KEY: misc_feature
<222> LOCATION: (9)..(9)
<223> OTHER INFORMATION: Xaa = Ala, or Ser
<220> FEATURE:
<221> NAME/KEY: misc_feature
<222> LOCATION: (12)..(12)
<223> OTHER INFORMATION: Xaa = Ala, or Ser
<220> FEATURE:
<221> NAME/KEY: misc_feature
<222> LOCATION: (13)..(13)
<223> OTHER INFORMATION: Xaa = Ala, or Val
<220> FEATURE:
<221> NAME/KEY: misc_feature
<222> LOCATION: (15)..(15)
```

```
<223> OTHER INFORMATION: Xaa = Leu, or Val
<220> FEATURE:
<221> NAME/KEY: misc_feature
<222> LOCATION: (17)..(17)
<223> OTHER INFORMATION: Xaa = Asp, Glu, or Gln
<220> FEATURE:
<221> NAME/KEY: misc_feature
<222> LOCATION: (19)..(19)
<223> OTHER INFORMATION: Xaa = Ala, or Val
<220> FEATURE:
<221> NAME/KEY: misc_feature
<222> LOCATION: (22)..(22)
<223> OTHER INFORMATION: Xaa = Asn, Ser, or Thr
<220> FEATURE:
<221> NAME/KEY: misc_feature
<222> LOCATION: (32)..(32)
<223> OTHER INFORMATION: Xaa = Asp, or Glu
<220> FEATURE:
<221> NAME/KEY: misc_feature
<222> LOCATION: (37)..(37)
<223> OTHER INFORMATION: Xaa = Leu, or Met
<220> FEATURE:
<221> NAME/KEY: misc_feature
<222> LOCATION: (46)..(46)
<223> OTHER INFORMATION: Xaa = Lys, or Gln
<220> FEATURE:
<221> NAME/KEY: misc_feature
<222> LOCATION: (64)..(64)
<223> OTHER INFORMATION: Xaa = Ala, Asp, or Ser
<220> FEATURE:
<221> NAME/KEY: misc_feature
<222> LOCATION: (78)..(78)
<223> OTHER INFORMATION: Xaa = Asn, or Thr
<220> FEATURE:
<221> NAME/KEY: misc_feature
<222> LOCATION: (80)..(80)
<223> OTHER INFORMATION: Xaa = His, or Ser
<220> FEATURE:
<221> NAME/KEY: misc_feature
<222> LOCATION: (81)..(81)
<223> OTHER INFORMATION: Xaa = Pro, or Ser
<220> FEATURE:
<221> NAME/KEY: misc_feature
<222> LOCATION: (82)..(82)
<223> OTHER INFORMATION: Xaa = Leu, or Val
<220> FEATURE:
<221> NAME/KEY: misc_feature
<222> LOCATION: (83)..(83)
<223> OTHER INFORMATION: Xaa = Glu, or Gln
<220> FEATURE:
<221> NAME/KEY: misc_feature
<222> LOCATION: (84)..(84)
<223> OTHER INFORMATION: Xaa = Ala, Glu, or Pro
<220> FEATURE:
<221> NAME/KEY: misc_feature
<222> LOCATION: (87)..(87)
<223> OTHER INFORMATION: Xaa = Ala, Phe, or Val
<220> FEATURE:
<221> NAME/KEY: misc_feature
<222> LOCATION: (89)..(89)
<223> OTHER INFORMATION: Xaa = Thr, or Val
<220> FEATURE:
<221> NAME/KEY: misc_feature
<222> LOCATION: (108)..(108)
<223> OTHER INFORMATION: Xaa = Leu, or Val

<400> SEQUENCE: 70

Asp Ile Xaa Leu Thr Gln Ser Pro Xaa Ser Leu Xaa Xaa Ser Xaa Gly
1               5                   10                  15

Xaa Arg Xaa Thr Ile Xaa Cys Lys Ala Ser Gln Ser Val Asp Tyr Xaa
            20                  25                  30

Gly Asp Ser Tyr Xaa Asn Trp Tyr Gln Gln Lys Pro Gly Xaa Pro Pro
        35                  40                  45

Lys Leu Leu Ile Tyr Ala Ala Ser Asn Leu Glu Ser Gly Ile Pro Xaa
    50                  55                  60
```

-continued

```
Arg Phe Ser Gly Ser Gly Ser Gly Thr Asp Phe Thr Leu Xaa Ile Xaa
65              70                  75                  80

Xaa Xaa Xaa Xaa Glu Asp Xaa Ala Xaa Tyr Tyr Cys Gln Gln Ser Asn
                85                  90                  95

Glu Asp Pro Ser Thr Phe Gly Gly Gly Thr Lys Xaa Glu Ile Lys
            100             105                 110

<210> SEQ ID NO 71
<211> LENGTH: 5
<212> TYPE: PRT
<213> ORGANISM: Artificial Sequence
<220> FEATURE:
<223> OTHER INFORMATION: Linker

<400> SEQUENCE: 71

Pro Val Gly Val Val
1               5
```